(12) United States Patent
Uzgiris et al.

(10) Patent No.: US 9,528,163 B2
(45) Date of Patent: Dec. 27, 2016

(54) REAGENTS AND METHODS FOR DETECTING HCV

(75) Inventors: Arejas Uzgiris, Berkeley, CA (US); Sunil Pandit, Concord, CA (US); Lance Palmer, Plainsboro, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 248 days.

(21) Appl. No.: 14/127,224

(22) PCT Filed: Jun. 20, 2012

(86) PCT No.: PCT/US2012/043312
§ 371 (c)(1),
(2), (4) Date: Dec. 18, 2013

(87) PCT Pub. No.: WO2012/177739
PCT Pub. Date: Dec. 27, 2012

(65) Prior Publication Data
US 2014/0134605 A1    May 15, 2014

Related U.S. Application Data

(60) Provisional application No. 61/498,870, filed on Jun. 20, 2011, provisional application No. 61/645,149, filed on May 10, 2012.

(51) Int. Cl.
*C12Q 1/70* (2006.01)

(52) U.S. Cl.
CPC .................... *C12Q 1/707* (2013.01)

(58) Field of Classification Search
None
See application file for complete search history.

(56) References Cited

U.S. PATENT DOCUMENTS

| 2003/0050470 | A1* | 3/2003 | An | C07H 21/00 536/24.3 |
|---|---|---|---|---|
| 2003/0175743 | A1* | 9/2003 | Ng | C12Q 1/689 435/6.16 |
| 2006/0286123 | A1* | 12/2006 | Fetzer | A61K 39/12 424/204.1 |
| 2007/0172926 | A1 | 7/2007 | Holland-Staley | |
| 2009/0220943 | A1 | 9/2009 | Hong et al. | |
| 2010/0311038 | A1 | 12/2010 | Vuagniaux et al. | |

FOREIGN PATENT DOCUMENTS

CN    WO 2005005658 A1 *  1/2005  ............. C12Q 1/701

OTHER PUBLICATIONS

Kasprowicz et al. Journal of Virology (2010) 84: 1656-1663.*
Fuller et al. Hepatology (2010) 51: 378-387.*
de Carvalho-Mello et al. Journal of General Virology (2010) 91: 691-696.*
Donlin et al. Journal of Virology (2007) 81: 8211-8224.*
GenBank Accession No. M62321; Sep. 5, 2007; [online] available at <http://www.ncbi.nlm.nih.gov/nuccore/m62321>; Retrieved on Jan. 12, 2015.*
GenBank Accession No. AY685593; Aug. 14, 2004; [online] available at <http://www.ncbi.nlm.nih.gov/nuccore/ay685593>; Retrieved on Jan. 12, 2015.*
Abd-Elsalam, K.A. Bioinformatic tools and guideline for PCR primer design. African Journal of Biotechnology 2003; 2: 91-95.*
Dieffenbach et al. General concepts for PCR primer design. PCR Methods and Applications 1993; 3: S30-S37.*
Choo et al. Genetic organization and diversity of the hepatitis C virus. Proceedings of the National Academy of Sciences, USA 1991; 88: 2451-2455.*
Allan Peres-Da-Silva et al; "Mutations in hepatitis C virus NS3 protease domain associated with resistance to specific protease inhibitors in antiviral therapy naive patients"; Archives of Virology; Official Journal of the Virology Division of the International Union of Microbiological Societies; 155(5): 807-811; (2010).
Lange C M et al; "HLA class I allele associations with HCV genetic variants in patients with chronic HCV genotypes 1a or 1b infection"; Journal of Hepatology; 53(6):1022-1028; (2010).
Lodrini S et al; "Sequence analysis of NS3 protease gene in clinical strains of hepatitis C virus"; Journal of Biological Regulators and Homeostatic Agents;17(2): 198-204; (2003).
Sheehy P et al; "A strategy for obtaining near full-length HCV cDNA clones (assemblicons) by assembly PCR"; Journal of Virological Methods, 123(2): 115-24; (2005).
Torres-Puente et al; "Using evolutionary tools to refine the new hypervariable region 3 within the envelope 2 protein of hepatitis C virus"; Infection, Genetics and Evolution; 8(1): 74-82; (2007).
Sarrazin C et al; "Dynamic Hepatitis C Virus Genotypic and Phenotypic Changes in Patients Treated with the Protease Inhibitor Telaprevir"; Gastroenterology; 132(5): 1767-1777; (2007).
Vallet Sophie et al; "Genetic heterogeneity of the NS3 protease gene in hepatitis C virus genotype 1 from untreated infected patients"; Journal of Medical Virology; 75(4): 528-537; (2005).
International Search Report for PCT/US2012/043312 dated Dec. 14, 2012.
Peres Da Silva, et al., Hepatitis C Virus Subtype 1a Isolate BR136 Polyprotein Gene, Partial cds; GenBank Accession GU126553; (2010); online available at <http://www.ncbi.nlm.nih.gov/nuccore/GU126553>; Retrieved on Nov. 23, 2012 (2 pages).
Li et al., Hepatitis C Virus Subtype 1a Isolate 570C_2598_4427_2 Polyprotein Gene, Partial cds; GenBank Accession HQ113619; (2010); online available at <http://www.ncbi.nlm.nih.gov/nuccore/HQ113619>; Retrieved on Nov. 23, 2012 (2 pages).

* cited by examiner

*Primary Examiner* — Angela M Bertagna

(57) ABSTRACT

The present disclosure relates to oligonucleotide sequences for amplification primers and their use in performing nucleic acid amplifications of HCV, in particular regions that encode the NS3 polypeptide. In some embodiments the primers are used in nested PCR methods for the detection or sequencing of HCV NS3. The oligonucleotide sequences are also provided assembled as kits that can be used to amplify and detect or sequence HCV NS3.

14 Claims, 4 Drawing Sheets

REAGENTS AND METHODS FOR DETECTING HCV

PRIORITY CLAIM

This application claims priority to U.S. Provisional Patent Application Ser. Nos. 61/498,870, filed Jun. 20, 2011 and 61/645,149, filed May 10, 2012; the entirety of both of which are hereby incorporated by reference.

This application incorporates by reference the sequence listing which is submitted together with this application in computer readable form which has the file name SequenceListing_2011P13250WOUS.txt and is 10 KB.

BACKGROUND

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 3.9 million infected people in the United States alone, according to the U.S. Center for Disease Control, roughly five times the number of people infected with the human immunodeficiency virus (HIV). According to the World Health Organization, there are more than 170 million infected individuals worldwide, with at least 3 to 4 million people being infected each year. Once infected, about 20% of people clear the virus, but the rest harbor HCV for the rest of their lives. Ten to twenty percent of chronically infected individuals eventually develop liver-destroying cirrhosis or cancer. The viral disease is transmitted parenterally by contaminated blood and blood products, contaminated needles, or sexually, and vertically from infected mothers or carrier mothers to their off-spring.

SUMMARY

The present disclosure relates to oligonucleotide sequences for amplification primers and their use in performing nucleic acid amplifications of HCV, in particular regions that encode the NS3 polypeptide. In some embodiments the primers are used in nested PCR methods for the detection or sequencing of HCV NS3. The oligonucleotide sequences are also provided assembled as kits that can be used to detect or sequence HCV NS3.

In some embodiments, isolated oligonucleotide amplification primers comprise a nucleic acid sequence selected from the group consisting of SEQ ID NOS: 1-20, complementary sequences thereof, active fragments thereof, and combinations thereof.

In some embodiments, collections of primers for amplifying a portion of HCV NS3 1a genomic sequence are provided which comprise one or more forward primers selected from the group consisting of SEQ ID NO: 1, SEQ ID NO: 2, SEQ ID NO: 3, SEQ ID NO: 4, SEQ ID NO: 5, active fragments thereof, and combinations thereof; and one or more reverse primers selected from the group consisting of SEQ ID NO: 6, SEQ ID NO: 7, SEQ ID NO: 8, SEQ ID NO: 9, SEQ ID NO: 10, active fragments thereof, and combinations thereof.

In some embodiments, collections of primers for amplifying a portion of HCV NS3 1b genomic sequence are provided which comprise one or more forward primers selected from the group consisting of SEQ ID NO: 11, SEQ ID NO: 12, SEQ ID NO: 13, SEQ ID NO: 14, SEQ ID NO: 15, active fragments thereof, and combinations thereof; and one or more reverse primers selected from the group consisting of SEQ ID NO: 16, SEQ ID NO: 17, SEQ ID NO: 18, SEQ ID NO: 19, SEQ ID NO: 20, active fragments thereof, and combinations thereof.

In some embodiments, kits for amplifying HCV NS3 by nested PCR are provided that comprise one of the aforementioned collections of primers as outer primers in combination with a suitable set of inner primers.

In some embodiments, methods of amplifying HCV NS3 in a sample are provided that comprise contacting a sample with one of the aforementioned collections of primers as outer primers and submitting the resulting mixture to a first nucleic acid amplification reaction. In some embodiments, these methods further comprise contacting a product from the first nucleic acid amplification reaction with a set of inner primers and submitting the resulting mixture to a second nucleic acid amplification reaction. In some embodiments, these methods further comprise sequencing a product from the second nucleic acid amplification reaction to detect an HCV NS3 polymorphism.

DEFINITIONS

Figure 1:
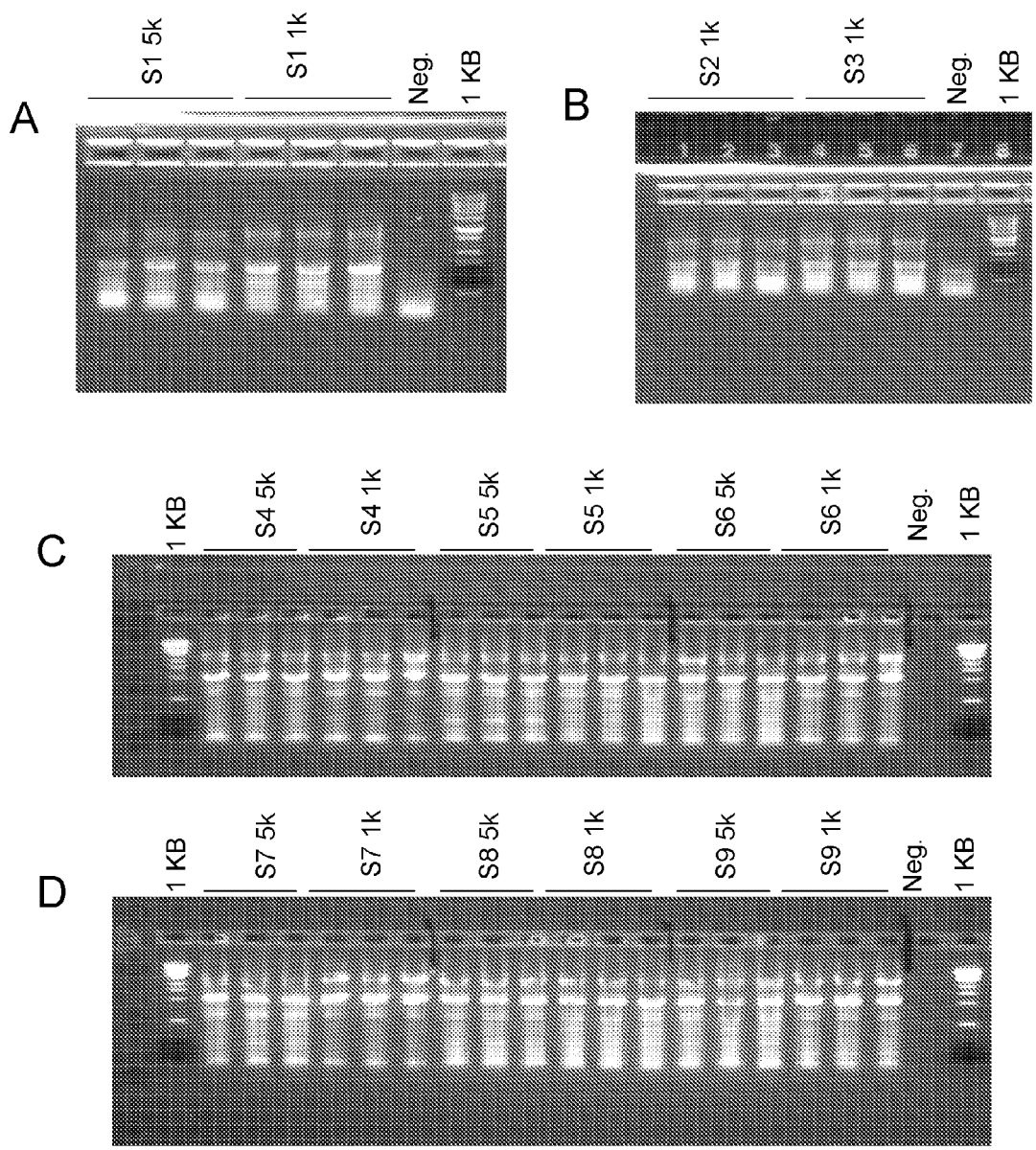
FIGS. 1A-D presents agarose gel electrophoretic profiles of first stage Reverse Transcriptase (RT) PCR amplification products of 9 HCV 1a clinical isolates (Samples S1-S9). Each reaction was run in triplicate at 1,000 and/or 5,000 copies/ml. Also included were negative controls lacking HCV and a 1 kb ladder.

The term "active fragment", as used herein in reference to an oligonucleotide (e.g., an oligonucleotide sequence provided herein), refers to any nucleic acid molecule which includes fewer nucleotides than the full length oligonucleotide, and retains at least one biological property of the full length oligonucleotide. For example, in some embodiments, active fragments may retain the ability to act as primers in an HCV amplification reaction. An active fragment of the present disclosure can be a nucleic acid molecule which is, for example, 10, 15, 20, 25, 30 or more nucleotides in length and can be used as a primer in an HCV amplification reaction.

The term "amplification" or "amplification reaction" is used herein to refer to any in vitro process for exponentially increasing the number of copies of a nucleotide sequence or sequences. Nucleic acid amplification results in the incorporation of nucleotides (ribonucleotides or deoxyribonucleotides) into primers to form DNA or RNA molecules that are complementary to a template nucleic acid molecule. As used herein, one amplification reaction may consist of many rounds of primer extension. For example, one PCR reaction may consist of several cycles of denaturation and extension ranging from, e.g., about 5 cycles to about 1000 cycles, or more.

The term "amplification reaction reagents", is used herein to refer to reagents used in nucleic acid amplification reactions and may include, but are not limited to, buffers, enzymes having reverse transcriptase and/or polymerase activity or exonuclease activity, enzyme cofactors such as magnesium or manganese, salts, nicotinamide adenine dinuclease (NAD) and deoxynucleoside triphosphates (dNTPs), such as deoxyadenosine triphosphate, deoxyguanosine triphosphate, deoxycytidine triphosphate and deoxythymidine triphosphate.

The term "gene", as used herein, has its art understood meaning, and refers to a part of the genome specifying a macromolecular product, be it DNA for incorporation into a host genome, a functional RNA molecule or a protein, and may include regulatory sequences (e.g., promoters, enhancers, etc.) and/or intron sequences preceding (5' non-coding sequences) and following (3' non-coding sequences) the coding sequences.

The term "hybridization", as used herein, refers to the formation of complexes (also called duplexes or hybrids) between nucleotide sequences which are sufficiently complementary to form complexes via Watson-Crick base pairing or non-canonical base pairing. It will be appreciated that hybridizing sequences need not have perfect complementary to provide stable hybrids. In many situations, stable hybrids will form where fewer than about 10% of the bases are mismatches. Accordingly, as used herein, the term "complementary" refers to a nucleic acid molecule that forms a stable duplex with its complement under assay conditions, generally where there is about 90% or greater homology (e.g., about 95% or greater, about 98% or greater, or about 99% or greater homology). Those skilled in the art understand how to estimate and adjust the stringency of hybridization conditions such that sequences that have at least a desired level of complementarity will stably hybridize, while those having lower complementarity will not. For examples of hybridization conditions and parameters, see, for example, Sambrook et al., *Molecular Cloning: A Laboratory Manual*, 1989, Second Edition, Cold Spring Harbor Press: Plainview, N.Y. and Ausubel, *Current Protocols in Molecular Biology*, 1994, John Wiley & Sons: Secaucus, N.J. Complementarity between two nucleic acid molecules is said to be "complete", "total" or "perfect" if all the nucleic acid's bases are matched, and is said to be "partial" otherwise.

The terms "labeled" and "labeled with a detectable agent (or moiety)" are used herein interchangeably to specify that an entity (e.g., a target sequence) can be visualized, e.g., directly or following hybridization to another entity that comprises a detectable agent or moiety. Preferably, the detectable agent or moiety is selected such that it generates a signal which can be measured and whose intensity is related to (e.g., proportional to) the amount of the entity of interest (e.g., a target sequence). Methods for labeling nucleic acid molecules are well-known in the art. In some embodiments, labeled nucleic acids can be prepared by incorporation of, or conjugation to, a label that is directly or indirectly detectable by spectroscopic, photochemical, biochemical, immunochemical, electrical, optical, or chemical means.

The term "melting temperature" or "Tm" of a specific oligonucleotide, as used herein, refers to the specific temperature at which half of the oligonucleotide hybridizes to its target in equilibrium. Accurate prediction of the Tm of any oligonucleotide can be made based on sequence using nearest neighbor parameter calculations.

The terms "nucleic acid", "nucleic acid molecule", "polynucleotide" or "oligonucleotide" are used herein interchangeably. They refer to linear polymers of nucleotide monomers or analogs thereof, such as deoxyribonucleic acid (DNA) and ribonucleic acid (RNA). Unless otherwise stated, the terms encompass nucleic acid-like structures with synthetic backbones, as well as amplification products. As will be appreciated by one skilled in the art, the length of these polymers (i.e., the number of nucleotides it contains) can vary widely, often depending on their intended function or use. In some embodiments, the term "oligonucleotide" is used herein to denote a polynucleotide that comprises between about 5 and about 150 nucleotides, e.g., between about 10 and about 100 nucleotides, between about 15 and about 75 nucleotides, or between about 15 and about 50 nucleotides. Throughout the specification, whenever an oligonucleotide is represented by a sequence of letters (chosen, for example, from the four base letters: A, C, G, and T, which denote adenosine, cytidine, guanosine, and thymidine, respectively), the nucleotides are presented in the 5'→3' order from the left to the right. In some embodiments, the sequence of an oligonucleotide of the present disclosure contains the letter Y and/or letter R and/or letter N and/or letter W and/or letter B. As used herein, the letter "Y" represents a degenerative base, which can be T or C with substantially equal probability. As used herein, the letter "R" represents a degenerative base, which can be A or G with substantially equal probability. As used herein, the letter "N" represents a degenerative base, which can be A or G or T or C. As used herein, the letter "W" represents a degenerative base, which can be A or T. As used herein, the letter "B" represents a degenerative base, which can be C or G or T. Thus, for example, in the context of the present disclosure, if an oligonucleotide contains one degenerative base M, the oligonucleotide is a substantially equimolar mixture of two subpopulations of a first oligonucleotide where the degenerative base is A and a second oligonucleotide where the degenerative base is C, the first and second oligonucleotides being otherwise identical.

The term "3'" refers to a region or position in a polynucleotide or oligonucleotide 3' (i.e., downstream) from another region or position in the same polynucleotide or oligonucleotide. The term "5'" refers to a region or position in a polynucleotide or oligonucleotide 5' (i.e., upstream) from another region or position in the same polynucleotide or oligonucleotide. The terms "3' end" and "3' terminus", as used herein in reference to a nucleic acid molecule, refer to the end of the nucleic acid which contains a free hydroxyl group attached to the 3' carbon of the terminal pentose sugar. The term "5' end" and "5' terminus", as used herein in reference to a nucleic acid molecule, refers to the end of the nucleic acid molecule which contains a free hydroxyl or phosphate group attached to the 5' carbon of the terminal pentose sugar.

The term "isolated", as used herein in reference to an oligonucleotide, means an oligonucleotide, which by virtue of its origin or manipulation, is separated from at least some of the components with which it is naturally associated or with which it is associated when initially obtained. By "isolated", it is alternatively or additionally meant that the oligonucleotide of interest is produced or synthesized by the hand of man.

The terms "primer", as used herein, typically refers to oligonucleotides that hybridize in a sequence specific manner to a complementary nucleic acid molecule (e.g., a nucleic acid molecule comprising a target sequence). In some embodiments, a primer will comprise a region of nucleotide sequence that hybridizes to at least about 8, e.g., at least about 10, at least about 15, or about 20 to about 40 consecutive nucleotides of a target nucleic acid (i.e., will hybridize to a contiguous sequence of the target nucleic acid). In general, a primer sequence is identified as being either "complementary" (i.e., complementary to the coding or sense strand (+)), or "reverse complementary" (i.e., complementary to the anti-sense strand (−)). In some embodiments, the term "primer" may refer to an oligonucleotide that acts as a point of initiation of a template-directed synthesis using methods such as PCR (polymerase chain reaction) or LCR (ligase chain reaction) under appropriate conditions (e.g., in the presence of four different nucleotide triphosphates and a polymerization agent, such as DNA polymerase, RNA polymerase or reverse-transcriptase, DNA ligase, etc., in an appropriate buffer solution containing any necessary reagents and at suitable temperature(s)). Such a template directed synthesis is also called "primer extension". For example, a primer pair may be designed to amplify a region of DNA using PCR. Such a pair will include a "forward primer" and a "reverse primer" that hybridize to complementary strands of a DNA molecule and that delimit a region to be synthesized and/or amplified.

The terms "forward primer" and "forward amplification primer" are used herein interchangeably, and refer to a primer that hybridizes (or anneals) to the target (template) strand. The terms "reverse primer" and "reverse amplification primer" are used herein interchangeably, and refer to a primer that hybridizes (or anneals) to the complementary target strand. The forward primer hybridizes with the target sequence 5' with respect to the reverse primer.

The term "primer set" is used herein to refer to two or more primers which together are capable of priming the amplification of a target nucleotide sequence (e.g., to amplify DNA or RNA encoding HCV NS3 or a portion thereof). In some embodiments, the term "primer set" refers to a pair of primers including a 5' (upstream) primer (or forward primer) that hybridizes with the 5'-end of the nucleic acid sequence to be amplified and a 3' (downstream) primer (or reverse primer) that hybridizes with the complement of the sequence to be amplified. Such primer set or primer pair are particularly useful in PCR amplification reactions.

As used herein, the term "nested primer set" refers to two or more primers which together are capable of priming the amplification of an amplified nucleotide sequence of interest. The primers in a "nested primer set" are sometimes referred to herein as "inner primers". In some embodiments, one or more primers of the "nested primer set" are overlapping with primers that were used to amplify the original nucleotide sequence of interest (i.e., with "outer primers"). In some embodiments, the "nested primer set" is non-overlapping with primers that were used to amplify the original nucleotide sequence of interest. In some embodiments, the term "nested primer set" refers to a pair of primers including a 5' (upstream) primer (or forward primer) that hybridizes with or towards the 5'-end of the amplified nucleic acid sequence of interest and a 3' (downstream) primer (or reverse primer) that hybridizes with or towards the 5'-end of the complement of the amplified nucleic acid sequence of interest.

As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, obtained cells are or include microbial cells of an individual's microbiome. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "secondary sample" or "processed sample" may comprise, for example nucleic acids or proteins extracted from a "primary sample" or obtained by subjecting a "primary sample" to techniques such as amplification or reverse transcription of mRNA, isolation and/or purification of certain components, etc.

The term "target nucleic acid sequence" or "nucleic acid of interest" is used herein to refer to any series of contiguous nucleotides in a template nucleic acid molecule (such as DNA, cDNA or RNA) to be amplified. One specific target nucleic acid sequence is a segment, region, or fragment of a nucleic acid molecule that hybridizes to at least one inner primer during a nested PCR reaction.

DETAILED DESCRIPTION OF SOME EMBODIMENTS

HCV is an enveloped, positive stranded RNA virus which has been classified as a separate genus within the Flavivirus family, e.g., see Heinz, *Arch. Virol.* (Suppl.) 4:163 (1992). The viral genome is approximately 9,500 nucleotides in length and contains one long open reading frame that encodes a precursor polyprotein of 330 Kd. Individual HCV polypeptides are produced by proteolytic processing of the precursor polypeptide. This proteolysis is catalyzed by a combination of both cellular and viral encoded proteases.

The organization and processing of the HCV polyprotein appears to be most similar to that of the pestiviruses. At least 10 polypeptides have been identified and the order of these cleavage products in the polyprotein is $NH_2$—C-E1-E2-p7-NS2-NS3-NS4A-NS4B—NS5A-NS5B—COOH. Proteolytic processing is mediated by host signal peptidase and two HCV-encoded proteinases, the NS2-3 autoproteinase and the NS3-4A serine proteinase. For further details see Rice, in "Fields Virology" (Fields et al., Eds.), pp. 931-960, Raven Press, New York (1996) and Shimotohno et al., *J. Hepatol.* 22: 87-92 (1995).

C is a basic protein that serves as the viral core or capsid protein; E1 and E2 are virion envelope glycoproteins; p7 is a hydrophobic protein of unknown function that is inefficiently cleaved from the E2 glycoprotein, e.g., see Mizushima et al., *J. Virol.* 68: 6215-6222 (1994) and Selby et al., *Virology* 204: 114-122 (1994). NS2 to NS5B are nonstructural (NS) proteins which function in viral RNA replication complexes. Their functions have been identified as follows: NS2 is a metalloprotease; NS3 is a protease/helicase that contains motifs characteristic of RNA helicases and that has been shown to possess an RNA-stimulated NTPase activity, e.g., see Suzich et al., *J. Virol.* 67, 6152-6158 (1993); NS4A is a co-factor for NS3; NS4B is of unknown function; NS5A interacts with cellular factors to transcriptionally modulate cellular genes and promote cell growth, e.g., see Ghosh et al., *J. Biol. Chem.* 275:7184-7188 (2000) and provide IFNα resistance; and NS5B is a replicase that contains the GDD motif characteristic of the RNA-dependent RNA polymerases of other positive-strand RNA viruses.

Several HCV polypeptides are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions.

I—Oligonucleotide Sequences and Amplification Primer Sets

Oligonucleotide Sequences

Previous research has identified subtypes of HCV with varying susceptibility to treatment. For example, pegylated-interferon in combination with Ribavirin, exhibits a sustained response rate of 40 to 50% across HCV patients. However, a majority of patients still do not elicit a sustained anti-viral response, particularly against the interferon-resistant HCV genotypes, 1a and 1b. The present disclosure provides oligonucleotide sequences that are specific for the 1a and 1b genotypes of the HCV NS3 gene.

Existing DNA sequencing assays for HCV NS3 region have limited performance due to the high variability of the HCV genome. The main mode of failure is due to poor performance of oligonucleotides meant to initiate reverse transcription followed by PCR based amplification of the viral RNA. There is a need to improve the sensitivity performance beyond what is currently possible.

Previous assays have not demonstrated sufficient performance to be widely accepted in clinical laboratories and have not been submitted for regulatory approval. Most are used as research assays or local home-brew laboratory developed tests due to these performance limitations. Previous assay designs have not solved these limitations.

The present disclosure, in contrast, results in uniquely high performing assay design prototypes. The top performing design meets IVD commercialization criteria of >95% successful amplification with known global sequence variants. This performance criteria has been previously demonstrated to be indicative of sufficient sensitivity across genetic variants to be implemented for routine clinical use with samples in international studies.

For the particular region targeted, HCV NS3, the design that was developed is likely to exhibit unique performance compared to other possible designs for the purpose of in vitro reverse transcription and PCR amplification of the entire NS3 coding region for genotype 1, subtypes 1a and 1b of HCV. This amplicon is considered the ideal material for further analysis by direct DNA sequencing, or nested PCR followed by DNA sequencing, to determine mutations associated with resistance to protease inhibitors in the NS3 region of HCV. It is also ideal for cloning and expression in model organisms for HCV disease studies and pharmaceutical development programs. The amplified patient-derived product may also be cloned for in vitro phenotyping experiments with pseudotyped virus.

The sequences of certain oligonucleotides of the present disclosure are set forth in Table 1 (SEQ ID NOS: 1-45).

TABLE 1

| SEQ ID NO. | Name | Sequence (5' → 3') | Strand |
|---|---|---|---|
| 1 | NS3_1a_1F | AGGGTGGAGGTTGCTGGC | (+) |
| 2 | NS3_1a_2F | GGGGTGGAGATTGCTGGC | (+) |
| 3 | NS3_1a_3F | GGGATGGAGGTTGCTGGC | (+) |
| 4 | NS3_1a_4F | GGGGTGGAGGTTGTTGGC | (+) |
| 5 | NS3_1a_5F | GGGGTGGAGGTTGCTGGC | (+) |
| 6 | NS3_1a_6R | GCCGGAACCTTGGTGCTCT | (−) |
| 7 | NS3_1a_7R | GCCGGGACTTTGGTGCTTT | (−) |
| 8 | NS3_1a_8R | GCTGGGACCTTGGTGCTCT | (−) |
| 9 | NS3_1a_9R | GCCGGGACCTTGGTGCTCT | (−) |
| 10 | NS3_1a_10R | GCCGGGACCTTGGTGCTTT | (−) |
| 11 | NS3_1b_1F | AGCCTCACAGGCCGGGAC | (+) |
| 12 | NS3_1b_2F | AGCCTTACAGGCCGGGAC | (+) |
| 13 | NS3_1b_3F | AGTCTCACAGGCCGGGAC | (+) |
| 14 | NS3_1b_4F | AGTCTCACAGGGCGGGAC | (+) |
| 15 | NS3_1b_5F | AGCCTCACAGGTCGGGAT | (+) |
| 16 | NS3_1b_6R | GCCACTTGGAATGTTTGCGG | (−) |
| 17 | NS3_1b_7R | GCCACTTGGAATGTCTGCGG | (−) |
| 18 | NS3_1b_8R | GCCACCTGGAATGTCTGCGG | (−) |
| 19 | NS3_1b_9R | GCCACTTGGAATGACTGCGG | (−) |
| 20 | NS3_1b_10R | GCCACTTGGAAAGTCTGCGG | (−) |
| 21 | SCR6.1 | GCTTGGGATATGATGATGAACTGGTC | (+) |
| 22 | SCR6.2 | GCGTGGGATATGATGATGAACTGGTC | (+) |
| 23 | SCR6.3 | GCATGGGATATGATGATGAACTGGTC | (+) |
| 24 | SCR6.4 | GCCTGGGATATGATGATGAACTGGTC | (+) |
| 25 | SCR8 | TGGGATATGATGATGAACTGGTC | (+) |
| 26 | SCR4.1 | AGGAACTTGCCGTAGGTGGAGTA | (−) |
| 27 | SCR4.2 | AGGAACTTGCCGTAGGTGGAATA | (−) |
| 28 | SCR4.3 | AGAAACTTGCCGTAGGTGGAGTA | (−) |

TABLE 1-continued

| SEQ ID NO. | Sequence Name | Sequence (5' → 3') | Strand |
|---|---|---|---|
| 29 | SCR4.4 | AGAAACTTGCCGTAGGTGGAGTA | (−) |
| 30 | SCR7.1 | AGGAACTTGCCGTAGGTGGA | (−) |
| 31 | SCR7.2 | AGGAACTTGCCATAGGTGGA | (−) |
| 32 | SCR7.3 | AGAAACTTGCCGTAGGTGGA | (−) |
| 33 | NS3-899s | GACTGGCCGGGACAARAACC | (+) |
| 34 | NS3-898as | GCTGGTGGRGAGGARTTGTC | (−) |
| 35 | NS3-892s | GTATCATCACYAGCCTCACRG | (+) |
| 36 | NS3-893as | CACTTGGAATGTYTGCGGTAC | (−) |
| 37 | BP_M13_Fwd | TTCTGGCGTACCGTTCCTGT | (+) |
| 38 | BP_M13_Rev | GTTTTCCCAGTCACGACGTTGTA | (−) |
| 39 | NS3_1a_F | RGGRTGGAGRTTGYTGGC | (+) |
| 40 | NS3_1a_R | GCYGGRACYTTGGTGCTYT | (−) |
| 41 | NS3_1b_F | AGYCTYACAGGBCGGGAY | (+) |
| 42 | NS3_1b_R | GCCACYTGGAAWGWYTGCGG | (−) |
| 43 | SCR6 | GCNTGGGATATGATGATGAACTGGTC | (+) |
| 44 | SCR4 | AGRAACTTGCCRTAGGTGGARTA | (−) |
| 45 | SCR7 | AGRAACTTGCCRTAGGTGGA | (−) |

In some embodiments, primers are degenerate primers encompassing the sequences of other primers. SEQ ID NO 39 comprises a degenerate primer sequence encompassing the sequences of SEQ ID NOS: 1-5. SEQ ID NO 40 comprises a degenerate primer sequence encompassing the sequences of SEQ ID NOS: 6-10. SEQ ID NO 41 comprises a degenerate primer sequence encompassing the sequences of SEQ ID NOS: 11-15. SEQ ID NO 42 comprises a degenerate primer sequence encompassing the sequences of SEQ ID NOS: 16-20. SEQ ID NO 43 comprises a degenerate primer sequence encompassing the sequences of SEQ ID NOS: 21-25. SEQ ID NO 44 comprises a degenerate primer sequence encompassing the sequences of SEQ ID NOS: 26-29. SEQ ID NO 45 comprises a degenerate primer sequence encompassing the sequences of SEQ ID NOS: 30-32.

Amplification Primer Sets

Oligonucleotides of the present disclosure may be conveniently provided as primer sets that can be used to amplify an HCV NS3 gene, e.g., to determine which polymorphic variant(s) is/are present among some or all of the possible polymorphic variants that may exist at a particular polymorphic site. Multiple sets of primers, capable of detecting polymorphic variants at a plurality of polymorphic sites are provided.

Examples of primer sets/pairs comprising a forward amplification primer and a reverse amplification primer include:

Primer Set 1, which comprises forward primers comprising all of SEQ ID NOS: 1-5 or any active fragments thereof and reverse primers comprising all of SEQ ID NOS: 6-10 or any active fragments thereof.

Primer Set 2, which comprises forward primers comprising all of SEQ ID NOS: 11-15 or any active fragments thereof and reverse primers comprising all of SEQ ID NOS: 16-20 or any active fragments thereof.

Primer Set 3, which comprises a forward primer comprising SEQ ID NO: 21 or any active fragment thereof and a reverse primer comprising SEQ ID NO: 26 or any active fragment thereof.

Primer Set 4, which comprises forward primers comprising all of SEQ ID NOS: 21-25 or any active fragments thereof and reverse primers comprising all of SEQ ID NOS: 26-29 or any active fragments thereof.

Primer Set 5, which comprises a forward primer comprising SEQ ID NO: 21 or any active fragment thereof and reverse primers comprising all of SEQ ID NOS: 26-29 or any active fragments thereof.

Primer Set 6, which comprises forward primers comprising all of SEQ ID NOS: 21-25 or any active fragments thereof and a reverse primer comprising SEQ ID NO: 26 or any active fragment thereof.

Primer Set 7, which comprises a forward primer comprising SEQ ID NO: 25 or any active fragment thereof and a reverse primer comprising SEQ ID NO: 30 or any active fragment thereof.

Primer Set 8, which comprises a forward primer comprising SEQ ID NO: 25 or any active fragment thereof and reverse primers comprising all of SEQ ID NOS: 30-32 or any active fragments thereof.

Primer Set 9, which comprises a forward primer comprising SEQ ID NO: 33 or any active fragment thereof and a reverse primer comprising SEQ ID NO: 34 or any active fragment thereof.

Primer Set 10, which comprises a forward primer comprising SEQ ID NO: 35 or any active fragment thereof and a reverse primer comprising SEQ ID NO: 36 or any active fragment thereof.

Primer Set 11, which comprises a forward primer comprising SEQ ID NO: 39 or any active fragment thereof and a reverse primer comprising SEQ ID NO: 40 or any active fragment thereof.

Primer Set 12, which comprises a forward primer comprising SEQ ID NO: 41 or any active fragment thereof and a reverse primer comprising SEQ ID NO: 42 or any active fragment thereof.

Primer Set 13, which comprises a forward primer comprising SEQ ID NO: 43 or any active fragment thereof and a reverse primer comprising SEQ ID NO: 44 or any active fragment thereof.

Primer Set 14, which comprises a forward primer comprising SEQ ID NO: 25 or any active fragment thereof and a reverse primer comprising SEQ ID NO: 45 or any active fragment thereof.

Oligonucleotide Preparation

Oligonucleotides of the present disclosure may be prepared by any of a variety of methods (see, e.g., Sambrook et al., "*Molecular Cloning: A Laboratory Manual*", 1989, $2^{nd}$ Ed., Cold Spring Harbour Laboratory Press: New York, N.Y.; "*PCR Protocols: A Guide to Methods and Applications*", 1990, Innis (Ed.), Academic Press: New York, N.Y.; Tijssen "*Hybridization with Nucleic Acid Probes—Laboratory Techniques in Biochemistry and Molecular Biology (Parts I and II)*", 1993, Elsevier Science; "*PCR Strategies*", 1995, Innis (Ed.), Academic Press: New York, N.Y.; and "*Short Protocols in Molecular Biology*", 2002, Ausubel (Ed.), $5^{th}$ Ed., John Wiley & Sons: Secaucus, N.J.).

In some embodiments, oligonucleotides may be prepared by chemical techniques well-known in the art, including, e.g., chemical synthesis and polymerization based on a template as described, e.g., in Narang et al., *Meth. Enzymol.* 68:90-98 (1979); Brown et al., *Meth. Enzymol.* 68: 109-151 (1979); Belousov et al., *Nucleic Acids Res.* 25:3440-3444 (1997); Guschin et al., *Anal. Biochem.* 250:203-211 (1997); Blommers et al., *Biochemistry* 33:7886-7896 (1994); Frenkel et al., *Free Radic. Biol. Med.* 19:373-380 (1995); and U.S. Pat. No. 4,458,066.

In some embodiments, oligonucleotides may be prepared using an automated, solid-phase procedure based on the phosphoramidite approach. In such methods, each nucleotide is individually added to the 5'-end of the growing oligonucleotide chain, which is attached at the 3'-end to a solid support. The added nucleotides are in the form of trivalent 3'-phosphoramidites that are protected from polymerization by a dimethoxytriyl (or DMT) group at the 5'-position. After base-induced phosphoramidite coupling, mild oxidation to give a pentavalent phosphotriester intermediate and DMT removal provides a new site for oligonucleotide elongation. The oligonucleotides are then cleaved off the solid support, and the phosphodiester and exocyclic amino groups are deprotected with ammonium hydroxide. These syntheses may be performed on oligo synthesizers such as those commercially available from Perkin Elmer/Applied Biosystems, Inc. (Foster City, Calif.), DuPont (Wilmington, Del.) or Milligen (Bedford, Mass.). Alternatively, oligonucleotides can be custom made and ordered from a variety of commercial sources well-known in the art, including, for example, the Midland Certified Reagent Company (Midland, Tex.), ExpressGen, Inc. (Chicago, Ill.), Operon Technologies, Inc. (Huntsville, Ala.), and many others.

Purification of oligonucleotides, where necessary or desirable, may be carried out by any of a variety of methods well-known in the art. For example, purification of oligonucleotides is typically performed either by native acrylamide gel electrophoresis, by anion-exchange HPLC, e.g., see Pearson and Regnier, *J. Chrom.* 255:137-149 (1983) or by reverse phase HPLC, e.g., see McFarland and Borer, *Nucleic Acids Res.* 7:1067-1080 (1979).

The sequence of oligonucleotides can be verified using any suitable sequencing method including, but not limited to, chemical degradation, e.g., see Maxam and Gilbert, *Methods of Enzymology,* 65:499-560 (1980), matrix-assisted laser desorption ionization time-of-flight (MALDI-TOF) mass spectrometry, e.g., see Pieles et al., *Nucleic Acids Res.* 21:3191-3196 (1993), mass spectrometry following a combination of alkaline phosphatase and exonuclease digestions, e.g., see Wu and Aboleneen, *Anal. Biochem.* 290:347-352 (2001).

The present disclosure encompasses modified versions of these oligonucleotides that perform as equivalents of these oligonucleotides in accordance with the methods of the present disclosure. These modified oligonucleotides may be prepared using any of several means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.), or charged linkages (e.g., phosphorothioates, phosphorodithioates, etc.). Modified oligonucleotide may also be derivatized by formation of a methyl or ethyl phosphotriester or an alkyl phosphoramidate linkage. Furthermore, the oligonucleotides of the present disclosure may also be modified with a label.

Labeling of Oligonucleotides

In some embodiments, the primers are labeled with a detectable agent or moiety before being used in amplification/detection assays. The role of a detectable agent is to allow visualization and detection of amplified target sequences. Preferably, the detectable agent is selected such that it generates a signal which can be measured and whose intensity is related (e.g., proportional) to the amount of amplification products in the sample being analyzed.

The association between the oligonucleotide and the detectable agent can be covalent or non-covalent. Labeled detection primers can be prepared by incorporation of or conjugation to a detectable moiety. Labels can be attached directly to the nucleic acid sequence or indirectly (e.g., through a linker). Linkers or spacer arms of various lengths are known in the art and are commercially available, and can be selected to reduce steric hindrance, or to confer other useful or desired properties to the resulting labeled molecules, e.g., see Mansfield et al., *Mol. Cell Probes* 9:145-156 (1995).

Various methods for labeling nucleic acid molecules are known in the art. For a review of labeling protocols, label detection techniques, and recent developments in the field, see, for example, Kricka, *Ann. Clin. Biochem.* 39:114-129 (2002); van Gijlswijk et al., *Expert Rev. Mol. Diagn.* 1:81-91 (2001); and Joos et al., *J. Biotechnol.* 35:135-153 (1994). Standard nucleic acid labeling methods include: incorporation of radioactive agents, direct attachments of fluorescent dyes (Smith et al., *Nucl. Acids Res.* 13:2399-2412 (1985)) or of enzymes (Connoly and Rider, *Nucl. Acids. Res.* 13:4485-4502 (1985)); chemical modifications of nucleic acid molecules making them detectable immunochemically or by other affinity reactions, e.g., see Broker et al., *Nucl. Acids Res.* 5:363-384 (1978); Bayer et al., *Methods of Biochem. Analysis* 26:1-45 (1980); Langer et al., *Proc. Natl. Acad. Sci. USA* 78:6633-6637 (1981); Richardson et al., *Nucl. Acids Res.* 11:6167-6184 (1983); Brigati et al., *Virol.* 126:32-50 (1983); Tchen et al., *Proc. Natl. Acad. Sci. USA* 81:3466-3470 (1984); Landegent et al., *Exp. Cell Res.* 15:61-72 (1984); and Hopman et al., *Exp. Cell Res.* 169:357-368 (1987); and enzyme-mediated labeling methods, such as random priming, nick translation, PCR and tailing with terminal transferase. For a review on enzymatic labeling, see, e.g., Temsamani and Agrawal, *Mol. Biotechnol.* 5:223-232 (1996). More recently developed nucleic acid labeling systems include, but are not limited to: ULS (Universal Linkage System), which is based on the reaction of mono-reactive cisplatin derivatives with the N7 position of guanine moieties in DNA (Heetebrij et al., *Cytogenet. Cell. Genet.* 87:47-52 (1999)), psoralen-biotin, which intercalates into nucleic acids and upon UV irradiation becomes covalently bonded to the nucleotide bases (Levenson et al., *Methods Enzymol.* 184:577-583 (1990); and Pfannschmidt et al., *Nucleic Acids Res.* 24:1702-1709 (1996)), photoreactive azido derivatives (Neves et al., *Bioconjugate Chem.* 11:51-55 (2000)), and DNA alkylating agents (Sebestyen et al., *Nat. Biotechnol.* 16: 568-576 (1998)).

It will be appreciated that any of a wide variety of detectable agents can be used in the practice of the present disclosure. Suitable detectable agents include, but are not limited to, various ligands, radionuclides (such as for example, $^{32}P$, $^{35}S$, $^{3}H$, $^{14}C$, $^{125}I$, $^{131}I$, and the like); fluorescent dyes; chemiluminescent agents (such as, for example, acridinium esters, stabilized dioxetanes, and the like); spectrally resolvable inorganic fluorescent semiconductor nanocrystals (i.e., quantum dots), metal nanoparticles (e.g., gold, silver, copper and platinum) or nanoclusters; enzymes (such as, for example, those used in an ELISA, e.g., horseradish peroxidase, beta-galactosidase, luciferase, alkaline phosphatase); colorimetric labels (such as, for example, dyes, colloidal gold, and the like); magnetic labels (such as, for example, Dynabeads™); and biotin, dioxigenin or other haptens and proteins for which antisera or monoclonal antibodies are available.

A "tail" of normal or modified nucleotides can also be added to tag an oligonucleotide for detectability purposes. In some embodiments, an M13 tag sequence (SEQ ID NO: 37 or 38) may be added.

II—Amplification Methods

In some embodiments, the present disclosure provides methods that use the aforementioned oligonucleotides as amplification primers to amplify regions of the HCV genome, in particular regions that encode the NS3 polypeptide. As discussed in more detail below, in some embodiments the primers are used in nested PCR methods for the amplification and detection or sequencing of HCV NS3.

Preparation of RNA

In some embodiments, the disclosed methods may involve some level of RNA preparation. Indeed, the template for an amplification reaction (e.g., a PCR reaction) is typically DNA and the target HCV material to be analyzed is typically expressed viral RNA. As a result, the starting template material for the amplification reaction will often be cDNA which was generated from purified RNA including RNA from viruses. The RNA preparation step may be performed far removed from the actual amplification step, for example, in another laboratory, or at a much earlier time; however, in some embodiments the RNA isolation and preparation of the cDNA may occur in conjunction with the amplification step of the methods.

When an RNA preparation step is included in the disclosed methods, the method of RNA preparation can be any method of RNA preparation that produces enzymatically manipulatable mRNA. For example, the RNA can be isolated by using the guanidinium isothiocyanate-ultracentrifugation method, the guanidinium and phenol-chloroform method, the lithium chloride-SDS-urea method or poly A+/mRNA from tissue lysates using oligo(dT) cellulose method, e.g., see Schildkraut et al., *J. Mol. Biol.* 4, 430-433 (1962); Chomczynski and Sacchi, *Anal. Biochem.* 162:156 (1987); Auffray and Rougeon, *Eur. J. Biochem.* 107:303-314 (1980); Aviv and Leder, *Proc. Natl. Acad. Sci. USA* 69, 1408-1412 (1972); and Sambrook et al., Selection of poly A+ RNA in "Molecular Cloning", Vol. 1, 7.26-7.29 (1989).

RNA can be isolated from any desired cell or cell type and from any organism, including mammals, such as mouse, rat, rabbit, dog, cat, monkey, and human, as well as other non-mammalian animals, such as fish or amphibians, as well as plants and even prokaryotes, such as bacteria. Thus, the DNA used in the method can also be from any organism, such as that disclosed for RNA.

Generation of cDNA

In some embodiments, disclosed methods involve cDNA preparation. The cDNA preparation step may be performed far removed from the actual amplification step, for example, in another laboratory, or at a much earlier time; however, in some embodiments the preparation of the cDNA may occur in conjunction with the amplification step of the methods.

When a cDNA preparation step is included in the disclosed methods, the method of cDNA preparation can be any method of cDNA preparation that produces enzymatically manipulatable cDNA. For example, the cDNA can be prepared by using, for example, random primers, poly-d(T) oligos, or NVd(T) oligos. For the purpose of data normalization, an equal amount of total RNA is typically used for cDNA synthesis. Many examples exist of performing reverse transcription to produce cDNA for use in PCR, including the following: Glisin et al., *Biochemistry* 13:2633-7 (1974); Ullrich et al., *Science* 196:1313 (1977); Chirgwin et al., *Biochemistry* 18:5294-9 (1979); Faulkner-Jones et al., *Endocrinol.* 133:2962-2972 (1993); and Gonda et al., *Mol. Cell Biol.* 2:617-624 (1982).

Reverse transcriptases from any source (native or recombinant) may be used in the practice of the present disclosure. Suitable reverse transcriptases include, but are not limited to, those from Moloney murine leukemia virus (M-MLV), human T-cell leukemia virus type I (HTLV-I), bovine leukemia virus (BLV), Avian Sarcoma Leukemia Viruses (ASLV) including Rous Sarcoma Virus (RSV) and Avian Myeloblastosis Virus (AMV), human immunodeficiency virus (HIV), cauliflower mosaic virus, *Saccharomyces, Neurospora, Drosophila*, primates, and rodents. See, for example, U.S. Pat. Nos. 4,663,290 and 6,063,60; Grandgenett, et al., *Proc. Nat. Acad. Sci. (USA)* 70:230-234 (1973), Gerard, *DNA* 5:271-279 (1986), Kotewicz, et al., *Gene* 35:249-258 (1985), Tanese et al., *Proc. Natl. Acad. Sci. (USA)* 82:4944-4948 (1985), Roth et al., *J. Biol. Chem.* 260:9326-9335 (1985), Michel et al., *Nature* 316:641-643 (1985), Akins et al., *Cell* 47:505-516 (1986) and *EMBO J.* 4:1267-75 (1985), and Fawcett, *Cell* 47:1007-1015 (1986); Shinnick et al., *Nature* 293:543-548 (1981); Seiki et al., *Proc. Natl. Acad. Sci. USA* 80:3618-3622 (1983); Rice et al., *Virology* 142:357-77 (1985); Schwartz et al., *Cell* 32:853-869 (1983); Larder et al., *EMBO J.* 6:3133-3137 (1987); Farmerie et al., *Science* 236:305-308 (1987); Barr et al., *Biotechnology* 5:486-489 (1987)); Tanese et al., *J. Virol.* 59:743-745 (1986); Hansen et al., *J. Biol. Chem.* 262:12393-12396 (1987); Sonigo et al., *Cell* 45:375-85 (1986); Takatsuji et al., *Nature* 319:240-243 (1986); Toh et al., *Nature* 305:827-829 (1983)); Alexander et al., *J. Virol.* 61:534-542 (1987); and Yuki et al., *Nucl. Acids Res.* 14:3017-3030 (1986).

Amplification Reaction

The use of oligonucleotide sequences of the present disclosure as primers to amplify HCV NS3 target sequences in test samples is not limited to any particular nucleic acid amplification technique or any particular modification thereof. In fact, the inventive oligonucleotide sequences can be employed in any of a variety of nucleic acid amplification methods well-known in the art (see, for example, Kimmel and Berger, *Methods Enzymol.* 152: 307-316 (1987); Sambrook et al., "*Molecular Cloning: A Laboratory Manual*", 1989, $2^{nd}$ Ed., Cold Spring Harbour Laboratory Press: New York, N.Y.; "*Short Protocols in Molecular Biology*", Ausubel (Ed.), 2002, $5^{th}$ Ed., John Wiley & Sons: Secaucus, N.J.).

Such nucleic acid amplification methods include, but are not limited to, the Polymerase Chain Reaction (or PCR, described, for example, in "*PCR Protocols: A Guide to Methods and Applications*", Innis (Ed.), 1990, Academic Press: New York; "*PCR Strategies*", Innis (Ed.), 1995, Academic Press: New York; "*Polymerase chain reaction: basic principles and automation in PCR: A Practical Approach*", McPherson et al. (Eds.), 1991, IRL Press: Oxford; Saiki et al., *Nature* 324:163 (1986); and U.S. Pat. Nos. 4,683,195, 4,683,202 and 4,889,818, each of which is incorporated herein by reference in its entirety); and reverse transcriptase polymerase chain reaction (or RT-PCR, described in, for example, U.S. Pat. Nos. 5,322,770 and 5,310,652).

The PCR (or polymerase chain reaction) technique is well-known in the art and has been disclosed, for example, in Mullis and Faloona, *Methods Enzymol.*, 155:350-355 (1987). In its simplest form, PCR is an in vitro method for the enzymatic synthesis of specific DNA sequences, using two primers that hybridize to opposite strands and flank the region of interest in the target DNA. A plurality of reaction cycles, each cycle comprising: a denaturation step, an annealing step, and a polymerization step, results in the exponential accumulation of a specific DNA fragment, see for example, "*PCR Protocols: A Guide to Methods and Applications*", Innis (Ed.), 1990, Academic Press: New York; "*PCR Strategies*", Innis (Ed.), 1995, Academic Press: New York; "*Polymerase chain reaction: basic principles and automation in PCR: A Practical Approach*", McPherson et al. (Eds.), 1991, IRL Press: Oxford; Saiki et al., *Nature* 324:163-166 (1986). The termini of the amplified fragments are defined as the 5' ends of the primers. Examples of DNA polymerases capable of producing amplification products in PCR reactions include, but are not limited to: *E. coli* DNA polymerase I, Klenow fragment of DNA polymerase I, T4 DNA polymerase, thermostable DNA polymerases isolated from *Thermus aquaticus* (Taq) which are available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). RNA target sequences may be amplified by reverse transcribing the mRNA into cDNA, and then performing PCR (RT-PCR), as described above. Alternatively, a single enzyme may be used for both steps as described in U.S. Pat. No. 5,322,770.

The duration and temperature of each step of a PCR cycle, as well as the number of cycles, are generally adjusted according to the stringency requirements in effect. Annealing temperature and timing are determined both by the efficiency with which a primer is expected to anneal to a template and the degree of mismatch that is to be tolerated. The ability to optimize the reaction cycle conditions is well within the knowledge of one of ordinary skill in the art. Although the number of reaction cycles may vary depending on the detection analysis being performed, it usually is at least 15, more usually at least 20, and may be as high as 60 or higher. However, in many situations, the number of reaction cycles typically ranges from about 20 to about 40.

The denaturation step of a PCR cycle generally comprises heating the reaction mixture to an elevated temperature and maintaining the mixture at the elevated temperature for a period of time sufficient for any double-stranded or hybridized nucleic acid present in the reaction mixture to dissociate. For denaturation, the temperature of the reaction mixture is usually raised to, and maintained at, a temperature ranging from about 85° C. to about 100° C., usually from about 90° C. to about 98° C., and more usually about 90° C. to about 94° C. for a period of time ranging from about 3 to about 120 seconds, usually from about 5 to about 30 seconds. In some embodiments, the first cycle is preceded by an elongated denaturation step ranging from about 1 to 10 minutes, usually from about 2 to 5 minutes.

Following denaturation, the reaction mixture is subjected to conditions sufficient for primer annealing to template DNA present in the mixture. The temperature to which the reaction mixture is lowered to achieve these conditions is usually chosen to provide optimal efficiency and specificity, and generally ranges from about 45° C. to about 75° C., usually from about 50° C. to about 70° C., and more usually from about 53° C. to about 55° C. Annealing conditions are generally maintained for a period of time ranging from about 15 seconds to about 30 minutes, usually from about 30 seconds to about 1 minute.

Following annealing of primer to template DNA or during annealing of primer to template DNA, the reaction mixture is subjected to conditions sufficient to provide for polymerization of nucleotides to the primer's end in a such manner that the primer is extended in a 5' to 3' direction using the DNA to which it is hybridized as a template (i.e., conditions sufficient for enzymatic production of primer extension product). To achieve primer extension conditions, the temperature of the reaction mixture is typically raised to a temperature ranging from about 65° C. to about 75° C., usually from about 67° C. to about 73° C., and maintained at that temperature for a period of time ranging from about 15 seconds to about 20 minutes, usually from about 30 seconds to about 5 minutes. In some embodiments, the final extension step is followed by an elongated extension step ranging from ranging from about 1 to 10 minutes, usually from about 2 to 5 minutes.

The above cycles of denaturation, annealing, and polymerization may be performed using an automated device typically known as a thermal cycler or thermocycler. Thermal cyclers that may be employed are described in U.S. Pat. Nos. 5,612,473; 5,602,756; 5,538,871; and 5,475,610. Thermal cyclers are commercially available, for example, from Perkin Elmer-Applied Biosystems (Norwalk, Conn.), Bio-Rad (Hercules, Calif.), Roche Applied Science (Indianapolis, Ind.), and Stratagene (La Jolla, Calif.).

In some embodiments, one or both of the PCR reactions are "kinetic PCR" (kPCR) or "kinetic RT-PCR" (kRT-PCR), which are also referred to as "real-time PCR" and "real-time RT-PCR," respectively. These methods involve detecting PCR products via a probe that provides a signal (typically a fluorescent signal) that is related to the amount of amplified product in the sample. Examples of commonly used probes used in kPCR and kRT-PCR include the following probes: TAQMAN® probes, Molecular Beacons probes, SCORPION® probes, and SYBR® Green probes. Briefly, TAQMAN® probes, Molecular Beacons, and SCORPION® probes each have a fluorescent reporter dye (also called a "fluor") attached to the 5' end of the probes and a quencher moiety coupled to the 3' end of the probes. In the unhybridized state, the proximity of the fluor and the quench molecules prevents the detection of fluorescent signal from the probe. During PCR, when the polymerase replicates a template on which a probe is bound, the 5'-nuclease activity of the polymerase cleaves the probe thus, increasing fluorescence with each replication cycle. SYBR® Green probes binds double-stranded DNA and upon excitation emit light; thus as PCR product accumulates, fluorescence increases.

In some embodiments, the PCR reaction is used in a "single-plex" PCR assay. "Single-plex" refers to a single assay that is not carried out simultaneously with any other assays. Single-plex assays include individual assays that are carried out sequentially.

In some embodiments, the PCR reaction is used in a "multiplex" PCR assay. The term "multiplex" refers to multiple assays that are carried out simultaneously, in which detection and analysis steps are generally performed in parallel. Within the context of the present disclosure, a multiplex assay will include the use of the primers, alone or in combination with additional primers to identify, for example, an HCV virus variant along with one or more additional HCV variants or other viruses.

In some embodiments, a first amplification step amplifies a region of a target gene. In some embodiments the amplification product is less than about 1500, 1400, 1300, 1200, 1100, 1000, 900, 800, 700, 600, 500, 400, 300, 250, 225, 200, 175 or 150 nucleotides long.

Nested PCR

In some embodiments, oligonucleotides of SEQ ID NOS: 1-36 and 39-45 can be used in a "nested" PCR reaction to accurately amplify the NS3 gene of HCV. A "nested" PCR reaction refers to a two-step specific amplification of a target nucleic acid. In the first amplification step, a segment of nucleic acid is amplified using a first (outer) primer set. In the second amplification step, a second (inner) primer set is used to further amplify a segment of the segment that was amplified in the first step. Both first- and second-step primer sets will flank the target nucleic acid. As a result, the final amplified product is obtained within the frame of the segment that was amplified in the first step. The present disclosure may be used in conjunction with any nested PCR system known to those of skill in the art to generate an amplified target nucleic acid sequence. In some embodiments, the methods can employ a reverse transcription step to produce cDNA, a first amplification step performed with a first primer set which is specific to a target sequence, a second amplification step performed with a second primer set on all or a portion of the first amplification mixture, and optionally a sequencing step to determine the sequence of the target sequence.

In some embodiments, forward primers for a first amplification step of nested PCR of the HCV NS3 gene are set forth in SEQ ID NOS: 21-25 and 43 or any active fragments or combinations thereof. In some embodiments, reverse primers for a first amplification step of nested PCR of the HCV NS3 gene are set forth in SEQ ID NOS: 26-32 and 44-45 or any active fragments or combinations thereof.

In some embodiments, forward primers for a first amplification step of nested PCR of the 1a genotype of the HCV NS3 gene are set forth in SEQ ID NOS: 1-5 and 39 or any active fragments or combinations thereof. In some embodiments, reverse primers for a first amplification step of nested PCR of the 1a genotype of the HCV NS3 gene are set forth in SEQ ID NOS: 6-10 and 40 or any active fragments or combinations thereof.

In some embodiments, forward primers for a first amplification step of nested PCR of the 1b genotype of the HCV NS3 gene are set forth in SEQ ID NOS: 11-15 and 41 or any active fragments or combinations thereof. In some embodiments, reverse primers for a first amplification step of nested PCR of the 1a genotype of the HCV NS3 gene are set forth in SEQ ID NOS: 16-20 and 42 or any active fragments or combinations thereof.

In some embodiments, the forward and reverse primers comprise an outer primer set for the first amplification step of HCV NS3. In some embodiments, this outer primer set comprises Primer sets 3-8, 13, or 14.

In some embodiments, the forward and reverse primers comprise an outer primer set for the first amplification step of the 1a genotype of HCV NS3. In some embodiments, this outer primer set comprises Primer set 1 or 11.

In some embodiments, the forward and reverse primers comprise an outer primer set for the first amplification step of 1b genotype of HCV NS3. In some embodiments, this outer primer set comprises Primer set 2 or 12.

A second round of PCR amplification, e.g., in order to ensure PCR specificity for the target sequence of interest, can be performed on the amplification product of the first amplification step. For instance, the amplicon, e.g., the HCV-specific amplicon, can be amplified in a PCR reaction with an inner primer set.

In some embodiments, forward primers for a second amplification step of nested PCR of the 1a genotype of the HCV NS3 gene are set forth in SEQ ID NOS: 1-5, 33, and 39 or any active fragments or combinations thereof. In some embodiments, reverse primers for a second amplification step of nested PCR of the 1a genotype of the HCV NS3 gene are set forth in SEQ ID NOS: 6-10, 34, and 40 or any active fragments or combinations thereof.

In some embodiments, forward primers for a second amplification step of nested PCR of the 1b genotype of the HCV NS3 gene are set forth in SEQ ID NOS: 11-15, 35, and 41 or any active fragments or combinations thereof. In some embodiments, reverse primers for a second amplification step of nested PCR of the 1a genotype of the HCV NS3 gene are set forth in SEQ ID NOS: 16-20, 36, and 42 or any active fragments or combinations thereof.

In some embodiments, the forward and reverse primers comprise an inner primer set for the second amplification step of the 1a genotype of HCV NS3. In some embodiments, this inner primer set comprises Primer sets 1, 9, or 11.

In some embodiments, the forward and reverse primers comprise an inner primer set for the second amplification step of the 1b genotype of HCV NS3. In some embodiments, this inner primer set comprises Primer sets 2, 10, or 12.

In some embodiments, the inner primer set is used to amplify an amplification product of the outer primer set. In some embodiments, the primers of the inner primer set are homologous to the amplification product of the outer primer set. In some embodiments, the inner primer set are homologous to the amplification product of the outer primer set and overlap with the outer primer set. In some embodiments, the inner primer set are homologous to the amplification product of the outer primer set and do not overlap with the outer primer set. In some embodiments, the outer primer set comprises Primer sets 3, 4, 5, 6, 7, 8, 13, or 14 and the inner primer set comprises Primer sets 1, 2, 11, or 12.

In some embodiments, the outer primer set comprises Primer set 1 or 11 and the inner primer set comprises Primer set 9. In some embodiments, the outer primer set comprises Primer set 2 or 12 and the inner primer set comprises Primer set 10.

Detection of Amplification Products

Amplification products generated using the oligonucleotides and methods of the present disclosure may be detected using a variety of methods known in the art.

In some embodiments, amplification products may simply be detected using agarose gel electrophoresis and visualization by ethidium bromide staining and exposure to ultraviolet (UV) light.

In some embodiments, the presence of a specific genotype can be shown by restriction enzyme analysis. For example, a specific nucleotide polymorphism can result in a nucleotide sequence comprising a restriction site which is absent from the nucleotide sequence of another allelic variant. Additionally or alternately, a specific nucleotide polymorphism can result in the elimination of a nucleotide sequence comprising a restriction site which is present in the nucleotide sequence of another allelic variant.

Examples of techniques for detecting differences of at least one nucleotide between two nucleic acids include, but are not limited to, selective oligonucleotide hybridization, selective amplification, or selective primer extension. For example, oligonucleotide probes may be prepared in which the known polymorphic nucleotide is placed centrally and then hybridized to target DNA under conditions which permit hybridization only if a perfect match is found, e.g., see Saiki et al., *Nature* 324:163 (1986); Saiki et al., *Proc.*

*Natl Acad. Sci USA* 86:6230 (1989); and Wallace et al., *Nucl. Acids Res.* 6:3543 (1979). Such specific oligonucleotide hybridization techniques may be used for the simultaneous detection of several nucleotide changes in different polymorphic regions of DNA. For example, oligonucleotides having nucleotide sequences of specific allelic variants are attached to a hybridizing membrane and this membrane is then hybridized with labeled sample nucleic acid. Analysis of the hybridization signal will then reveal the identity of the nucleotides of the sample nucleic acid. Alternatively unlabeled sample nucleic acid may be immobilized and contacted with labeled oligonucleotides that hybridize selectively with specific allelic variants.

Real-time pyrophosphate DNA sequencing is yet another approach to detection of polymorphisms and polymorphic variants, e.g., see Alderborn et al., *Genome Research,* 10(8): 1249-1258 (2000). Additional methods include, for example, PCR amplification in combination with denaturing high performance liquid chromatography (dHPLC), e.g., see Underhill et al., *Genome Research,* 7(10):996-1005 (1997).

In some embodiments, any of a variety of sequencing reactions known in the art can be used to directly sequence at least a portion of amplified DNA and detect allelic variants. The sequence can be compared with the sequences of known allelic variants to determine which one(s) are present in the sample. Exemplary sequencing reactions include those based on techniques developed by Maxam and Gilbert, *Proc. Natl. Acad. Sci USA,* 74:560 (1977) or Sanger, *Proc. Nat. Acad. Sci* 74:5463 (1977). It is also contemplated that any of a variety of automated sequencing procedures may be utilized when performing the subject assays, e.g., see Venter et al., *Science,* 291:1304-1351 (2001); Lander et al., *Nature,* 409:860-921 (2001), including sequencing by mass spectrometry, e.g., see U.S. Pat. No. 5,547,835 and PCT Patent Publication No. WO 94/16101 and WO 94/21822; U.S. Pat. No. 5,605,798 and PCT Patent Application No. PCT/US96/03651; Cohen et al., *Adv. Chromatogr.* 36:127-162 (1996); and Griffin et al., *Appl. Biochem. Biotechnol.* 38:147-159 (1993). It will be evident to one skilled in the art that, for some embodiments, the occurrence of only one, two or three of the nucleic acid bases need be determined in the sequencing reaction. Yet other sequencing methods are disclosed, e.g., in U.S. Pat. Nos. 5,580,732; 5,571,676; 4,863,849; 5,302,509; PCT Patent Application Nos. WO 91/06678 and WO 93/21340; Canard et al., *Gene* 148:1-6 (1994); Metzker et al., *Nucleic Acids Research* 22:4259-4267 (1994) and U.S. Pat. Nos. 5,740,341 and 6,306,597.

III—Kits

In some embodiments, the present disclosure provides kits comprising materials useful for the amplification and detection or sequencing of HCV NS3 according to methods described herein. The inventive kits may be used by diagnostic laboratories, experimental laboratories, or practitioners.

Materials and reagents useful for the detection or sequencing of HCV NS3 according to the present disclosure may be assembled together in a kit. In some embodiments, an inventive kit comprises at least one inventive primer set, and optionally, reverse transcription and/or amplification reaction reagents. In some embodiments, a kit comprises reagents which render the procedure specific. Thus, a kit intended to be used for the detection of a particular HCV variant (e.g., 1a or 1b) preferably comprises primer sets described herein that can be used to amplify a particular HCV target sequence of interest. A kit intended to be used for the multiplex detection of a plurality of HCV target sequences and/or other viruses preferably comprises a plurality of primer sets (optionally in separate containers) described herein that can be used to amplify HCV target sequences described herein.

Suitable reverse transcription/amplification reaction reagents that can be included in an inventive kit include, for example, one or more of: buffers; enzymes having reverse transcriptase and/or polymerase activity; enzyme cofactors such as magnesium or manganese; salts; nicotinamide adenide dinuclease (NAD); and deoxynucleoside triphosphates (dNTPs) such as, for example, deoxyadenosine triphospate; deoxyguanosine triphosphate, deoxycytidine triphosphate and deoxythymidine triphosphate, biotinylated dNTPs, suitable for carrying out the amplification reactions.

Depending on the procedure, the kit may further comprise one or more of: wash buffers and/or reagents, hybridization buffers and/or reagents, labeling buffers and/or reagents, and detection means. The buffers and/or reagents included in a kit are preferably optimized for the particular amplification/detection technique for which the kit is intended. Protocols for using these buffers and reagents for performing different steps of the procedure may also be included in the kit.

Furthermore, the kits may be provided with an internal control as a check on the amplification procedure and to prevent occurrence of false negative test results due to failures in the amplification procedure. An optimal control sequence is selected in such a way that it will not compete with the target nucleic acid sequence in the amplification reaction (as described above).

Kits may also contain reagents for the isolation of nucleic acids from biological specimen prior to amplification and/or for the purification or separation of HCV before nucleic acid extraction.

The reagents may be supplied in a solid (e.g., lyophilized) or liquid form. The kits of the present disclosure optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the amplification/detection assay may also be provided. The individual containers of the kit are preferably maintained in close confinement for commercial sale.

The kit may also comprise instructions for using the amplification reaction reagents and primer sets or primer/probe sets according to the present disclosure. Instructions for using the kit according to one or more methods of the present disclosure may comprise instructions for processing the biological sample, extracting nucleic acid molecules, and/or performing the test; instructions for interpreting the results as well as a notice in the form prescribed by a governmental agency (e.g., FDA) regulating the manufacture, use or sale of pharmaceuticals or biological products.

EXAMPLES

Example 1

Nested PCR on NS3 Gene of HCV 1a

An assay was carried out to perform nested PCR on the NS3 gene of the 1a variant of HCV.

Viral RNA was extracted from 8 clinical samples using the QIAmp Viral RNA Kit (Qiagen). 140 μl of sample was used.

Reverse transcription (RT) PCR was then performed isolated HCV virus. 37.8 μl nuclease free water, 23.6 μl dNTPs, 15.8 μl DTT, 4.7 μl of a 30 μM equimolar mixture of SEQ ID NOS: 1-5, 4.7 μl of a 30 μM equimolar mixture of SEQ ID NOS: 6-10, and 7.9 μl of RNAse Inhibitor (Applied Biosciences) were combined to create a first master mix. 6 μl of the first master mix was added to 20 μl of the viral template for each clinical sample and the reaction was heated in the thermocycler for 2 minutes at 90° C. and then 5 minutes at 52° C.

14 μl of a second master mix containing 157.5 μl RT-PCR Buffer, 7.9 μl RNAse Inhibitor (Applied Biosciences), 15.8 μl Superscript III Reverse Transcriptase (Invitrogen) and 39.4 μl DNA polymerase, was then added to the reaction, resulting in a final concentration of 1,000 or 5,000 U/ml of the viral template. The RT reaction was completed by an additional 35 minute incubation at 52° C. followed by 2 minutes at 94° C.

The PCR reaction then commenced immediately with 37 cycles of a 30 second denaturation step at 94° C. followed by a 30 second annealing step at 53° C. followed by a 2 minute extension step at 68° C. The last cycle was followed by an additional 2 minute extension step at 68° C. and hold step at 4° C.

The RT-PCR product was run on an agarose gel to visualize the product. 15 μl E-gel load dye was mixed with 5 μl of the amplification product and run on a gel for 30 minutes followed by visualization with UV light (see FIG. 1).

The nested PCR reaction was performed on the amplification products from the RT-PCR reaction. 1590 nuclease free water, 300 μl 10×PCR buffer, 60 μl 10 mM dNTPs, 120 μl 25 mM MgCl$_2$, 300 μl 1 μM SEQ ID NO: 33, 300 μl 1 μM SEQ ID NO: 34, and 30 μl 5U/μl AmpliTaq Gold (Applied Biosystems) were combined to create a master mix. 45 μl of master mix was added to 5 μl of a 1:10 dilution of the RT-PCR amplification product.

The PCR reaction consisted of an initial 5 minute denaturation at 94° C. followed by 35 cycles of a 30 second denaturation step at 94° C. followed by a 30 second annealing step at 55° C. followed by a 2 minute extension step at 72° C. The last cycle was followed by an additional 2 minute extension step at 72° C. and hold step at 4° C.

Figure 2:
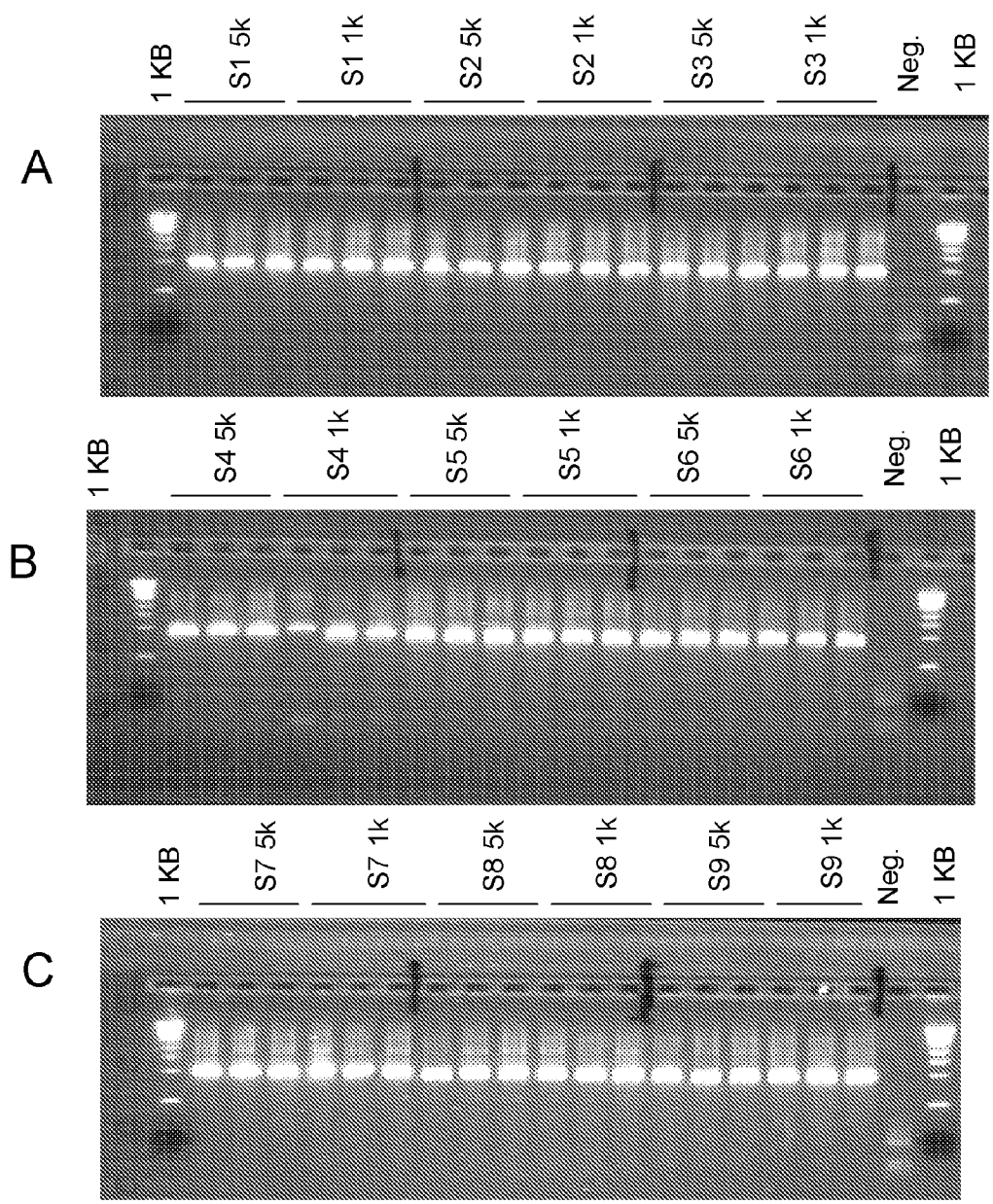
FIGS. 2A-C presents agarose gel electrophoretic profiles of a second stage nested PCR amplification products of 9 HCV 1a clinical isolates (Samples S1-S9). Each reaction was run in triplicate and the starting template was the amplification product of a RT PCR reaction with 1,000 and/or 5,000 copies of HCV/ml. Also included were negative controls lacking HCV and a 1 kb ladder.

Nested PCR products were examined by gel electrophoresis and subject to sequence analysis. FIG. 2 presents agarose gel electrophoresis profiles of samples taken after the second step of nested PCR.

Example 2

Nested PCR on NS3 Gene of HCV 1b

An assay was carried out to perform nested PCR on the NS3 gene of the 1b variant of HCV.

Viral RNA was extracted from 6 clinical samples using the QIAmp Viral RNA Kit (Qiagen). 140 μl of sample was used.

Reverse Transcription (RT) PCR was then performed isolated HCV virus. 57.6 μl nuclease free water, 36 μl dNTPs, 24 μl DTT, 7.2 μl of a 30 μM equimolar mixture of SEQ ID NOS: 11-15, 7.2 μl of a 30 μM equimolar mixture of SEQ ID NOS: 16-20, and 12 μl of RNAse Inhibitor (Applied Biosciences) were combined to create a first master mix. 6 μl of the first master mix was added to 20 μl of the viral template for each clinical sample and the reaction was heated in the thermocycler for 2 minutes at 90° C. and then 5 minutes at 52° C.

14 μl of a second master mix containing 240 μl RT-PCR Buffer, 12 μl RNAse Inhibitor (Applied Biosciences), 24 μl Superscript III Reverse Transcriptase (Invitrogen) and 60 μl DNA polymerase, was then added to the reaction, resulting in a final concentration of 10,000 or 5,000 U/ml of the viral template. The RT reaction was completed by an additional 35 minute incubation at 52° C. followed by 2 minutes at 94° C.

The PCR reaction then commenced immediately with 37 cycles of a 30 second denaturation step at 94° C. followed by a 30 second annealing step at 53° C. followed by a 2 minute extension step at 68° C. The last cycle was followed by an additional 2 minute extension step at 68° C. and hold step at 4° C.

Figure 3:
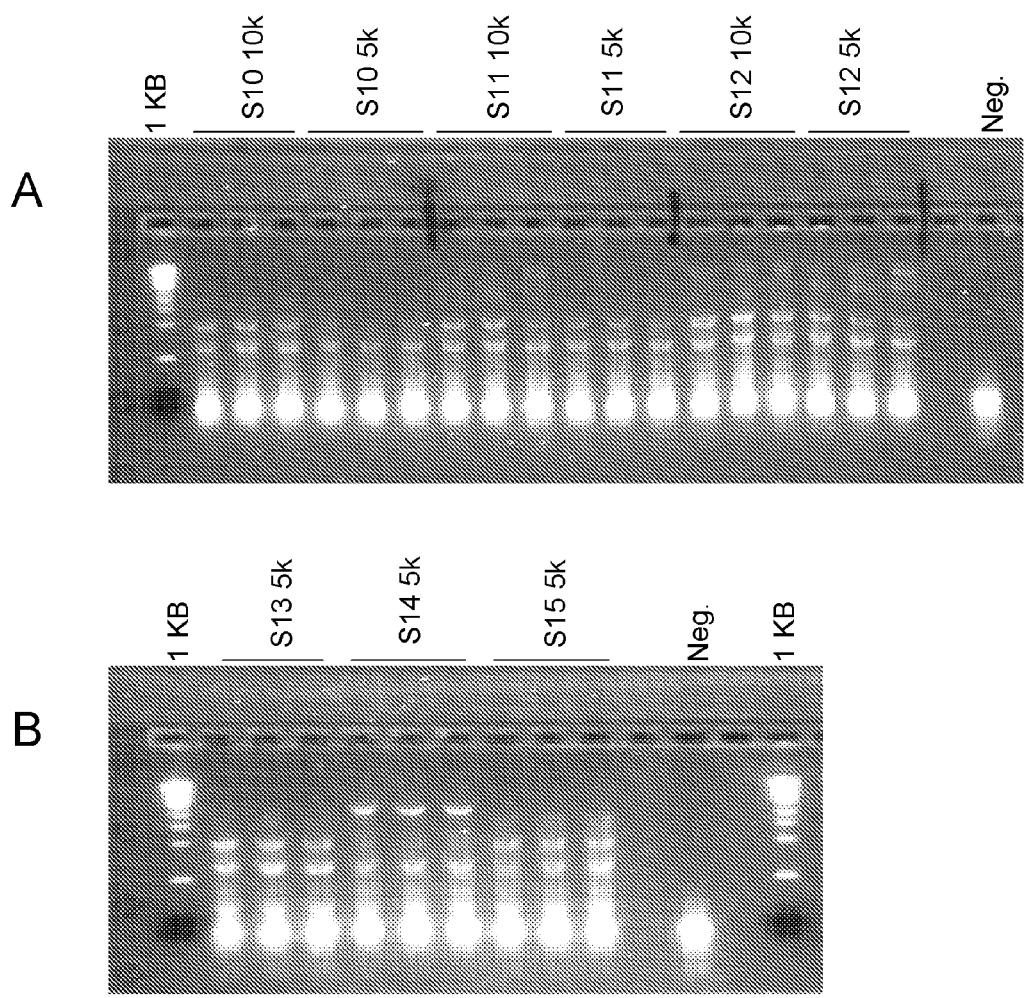
FIGS. 3A-B presents agarose gel electrophoretic profiles of first stage RT PCR amplification products of 6 HCV 1b clinical isolates (Samples S10-S15). Each reaction was run in triplicate at 10,000 and/or 5,000 copies/ml. Also included were negative controls lacking HCV and a 1 kb ladder.

The RT-PCR product was run on an agarose gel to visualize the product. 15 μl E-gel load dye was mixed with 5 μl of the amplification product and run on a gel for 30 minutes followed by visualization with UV light (see FIG. 3).

The nested PCR reaction was performed on the amplification products from the RT-PCR reaction. 1590 nuclease free water, 300 μl 10× PCR buffer, 60 μl 10 mM dNTPs, 120 μl 25 mM MgCl2, 300 μl 1 μM SEQ ID NO: 35, 300 μl 1 μM SEQ ID NO: 36, and 30 μl 5U/μl AmpliTaq Gold (Applied Biosystems) were combined to create a master mix. 45 μl of master mix was added to 5 μl of a 1:10 dilution of the RT-PCR amplification product.

The PCR reaction consisted of an initial 5 minute denaturation at 94° C. followed by 35 cycles of a 30 second denaturation step at 94° C. followed by a 30 second annealing step at 52° C. followed by a 2 minute extension step at 72° C. The last cycle was followed by an additional 2 minute extension step at 72° C. and hold step at 4° C.

Figure 4:
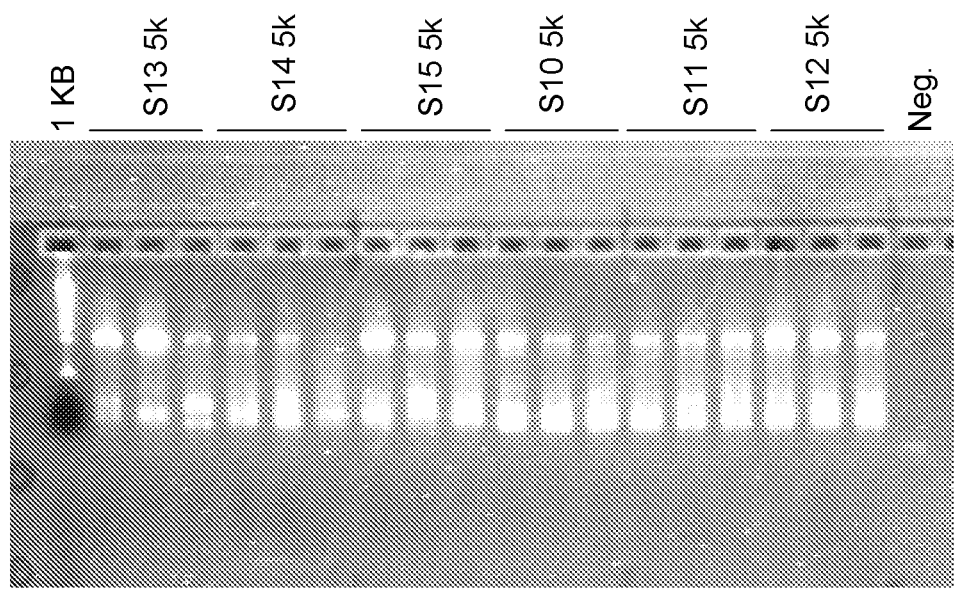
FIG. 4 presents agarose gel electrophoretic profiles of second stage nested PCR amplification products of 6 HCV 1b clinical isolates (Samples S10-S15). Each reaction was run in triplicate and the starting template was the amplification product of a RT PCR reaction with 5,000 copies of HCV/ml. Also included were negative controls lacking HCV and a 1 kb ladder.

Nested PCR products were examined by gel electrophoresis and subject to sequence analysis. FIG. 4 presents agarose gel electrophoresis profiles of samples taken after the second step of nested PCR.

EQUIVALENTS

Those skilled in the art will recognize, or be able to ascertain using no more than routine experimentation, many equivalents to the specific embodiments of the inventions described herein. The scope of the present disclosure is not intended to be limited to the scope of the above description, but rather is as set forth in the following claims.

What is claimed is:

1. A collection of primers for amplifying a portion of an HCV NS3 1a genomic sequence comprising:
   one or more forward primers each comprising a nucleic acid sequence selected from the group consisting of:
   (i) SEQ ID NO: 1,
   (ii) SEQ ID NO: 2 or an active fragment thereof,
   (iii) SEQ ID NO: 3 or an active fragment thereof, and
   (iv) SEQ ID NO: 4; and
   one or more reverse primers each comprising a nucleic acid sequence selected from the group consisting of:
   (i) SEQ ID NO: 6 or an active fragment thereof,
   (ii) SEQ ID NO: 7 or an active fragment thereof,
   (iii) SEQ ID NO: 8 or an active fragment thereof, and
   (iv) SEQ ID NO: 9;
   wherein the one or more forward primers and the one or more reverse primers are deoxyribonucleic acid primers, and wherein an active fragment is 15 or more nucleotides in length.

2. A collection of primers for amplifying a portion of an HCV NS3 1a genomic sequence, wherein the collection of primers comprises forward primers and reverse primers, the forward primers comprising: a primer comprising SEQ ID NO: 1 or an active fragment thereof, a primer comprising SEQ ID NO: 2 or an active fragment thereof, a primer comprising SEQ ID NO: 3 or an active fragment thereof, a primer comprising SEQ ID NO: 4 or an active fragment thereof, and a primer comprising SEQ ID NO: 5 or an active fragment thereof, and the reverse primers comprising a primer comprising SEQ ID NO: 6 or an active fragment thereof, a primer comprising SEQ ID NO: 7 or an active fragment thereof, a primer comprising SEQ ID NO: 8 or an active fragment thereof, a primer comprising SEQ ID NO: 9 or an active fragment thereof, and a primer comprising SEQ ID NO: 10 or an active fragment thereof.

3. A kit for amplifying HCV NS3 by nested PCR comprising a set of inner primers and a set of outer primers, wherein the set of outer primers comprises a collection of primers as defined in claim 1.

4. A kit for amplifying HCV NS3 by nested PCR comprising a set of inner primers and a set of outer primers, wherein the set of outer primers comprises a collection of primers as defined in claim 2.

5. The kit of claim 3, wherein at least some of the inner primers are labeled with a detectable moiety.

6. The kit of claim 3, wherein at least some of the inner primers are tagged with tag sequences.

7. The kit of claim 6, wherein the tag sequences are M13 tag sequences.

8. A method of amplifying HCV NS3 in a sample comprising contacting a sample with a set of outer primers, wherein the set of outer primers comprises the collection of primers of claim 1 and submitting the resulting mixture to a first nucleic acid amplification reaction.

9. The method of claim 8, further comprising contacting a product from the first nucleic acid amplification reaction with a set of inner primers and submitting the resulting mixture to a second nucleic acid amplification reaction.

10. The method of claim 8, wherein the set of outer primers comprises a collection of primers as defined in claim 2.

11. The method of claim 9, wherein at least some of the inner primers are labeled.

12. The method of claim 9, wherein at least some of the inner primers are tagged with tag sequences.

13. The method of claim 12, wherein the tag sequences are M13 tag sequences.

14. The method of claim 9, further comprising sequencing a product from the second nucleic acid amplification reaction to detect an HCV NS3 polymorphism.

* * * * *

UNITED STATES PATENT AND TRADEMARK OFFICE
CERTIFICATE OF CORRECTION

PATENT NO. : 9,528,163 B2
APPLICATION NO. : 14/127224
DATED : December 27, 2016
INVENTOR(S) : Arejas Uzgiris, Sunil Pandit and Lance Palmer Page 1 of 1

It is certified that error appears in the above-identified patent and that said Letters Patent is hereby corrected as shown below:

In the Specification

Column 2, Line 24, please replace "Figures 1 A-D presents" with "Figure 1, panels A-D, present".

Column 2, Line 30, please replace "Figures 2 A-C presents" with "Figure 2, panels A-C, present".

Column 2, Line 37, please replace "Figures 3 A-B presents" with "Figure 3, panels A and B, present".

Column 21, Line 26, please replace "(see Figure 1)" with "(see Figure 1, panels A-D)".

Column 21, Line 43, please replace "Figure 2 presents" with "Figure 2, panels A-C, present".

Column 22, Line 27, please replace "(see Figure 3)" with "(see Figure 3, panels A and B)".

Signed and Sealed this
Fourth Day of July, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 45

<210> SEQ ID NO 1
<211> LENGTH: 18
<212> TYPE: DNA
<213> ORGANISM: Artificial Sequence
<220> FEATURE:
<223> OTHER INFORMATION: Forward primer for HCV 1a
```

<400> SEQUENCE: 1
agggtggagg ttgctggc                                             18

<210> SEQ ID NO 2
<211> LENGTH: 18
<212> TYPE: DNA
<213> ORGANISM: Artificial Sequence
<220> FEATURE:
<223> OTHER INFORMATION: Forward primer for HCV 1a

<400> SEQUENCE: 2
ggggtggaga ttgctggc                                             18

<210> SEQ ID NO 3
<211> LENGTH: 18
<212> TYPE: DNA
<213> ORGANISM: Artificial Sequence
<220> FEATURE:
<223> OTHER INFORMATION: Forward primer for HCV 1a

<400> SEQUENCE: 3
gggatggagg ttgctggc                                             18

<210> SEQ ID NO 4
<211> LENGTH: 18
<212> TYPE: DNA
<213> ORGANISM: Artificial Sequence
<220> FEATURE:
<223> OTHER INFORMATION: Forward primer for HCV 1a

<400> SEQUENCE: 4
ggggtggagg ttgttggc                                             18

<210> SEQ ID NO 5
<211> LENGTH: 18
<212> TYPE: DNA
<213> ORGANISM: Artificial Sequence
<220> FEATURE:
<223> OTHER INFORMATION: Forward primer for HCV 1a

<400> SEQUENCE: 5
ggggtggagg ttgctggc                                             18

<210> SEQ ID NO 6
<211> LENGTH: 19
<212> TYPE: DNA
<213> ORGANISM: Artificial Sequence
<220> FEATURE:
<223> OTHER INFORMATION: Reverse primer for HCV 1a

<400> SEQUENCE: 6
gccggaacct tggtgctct                                            19

<210> SEQ ID NO 7
<211> LENGTH: 19
<212> TYPE: DNA
<213> ORGANISM: Artificial Sequence
<220> FEATURE:
<223> OTHER INFORMATION: Reverse primer for HCV 1a

<400> SEQUENCE: 7
gccgggactt tggtgctttt                                           19

<210> SEQ ID NO 8

```
<211> LENGTH: 19
<212> TYPE: DNA
<213> ORGANISM: Artificial Sequence
<220> FEATURE:
<223> OTHER INFORMATION: Reverse primer for HCV 1a

<400> SEQUENCE: 8
gctgggacct tggtgctct                                                19

<210> SEQ ID NO 9
<211> LENGTH: 19
<212> TYPE: DNA
<213> ORGANISM: Artificial Sequence
<220> FEATURE:
<223> OTHER INFORMATION: Reverse primer for HCV 1a

<400> SEQUENCE: 9
gccgggacct tggtgctct                                                19

<210> SEQ ID NO 10
<211> LENGTH: 19
<212> TYPE: DNA
<213> ORGANISM: Artificial Sequence
<220> FEATURE:
<223> OTHER INFORMATION: Reverse primer for HCV 1a

<400> SEQUENCE: 10
gccgggacct tggtgcttt                                                19

<210> SEQ ID NO 11
<211> LENGTH: 18
<212> TYPE: DNA
<213> ORGANISM: Artificial Sequence
<220> FEATURE:
<223> OTHER INFORMATION: Forward primer for HCV 1b

<400> SEQUENCE: 11
agcctcacag gccgggac                                                 18

<210> SEQ ID NO 12
<211> LENGTH: 18
<212> TYPE: DNA
<213> ORGANISM: Artificial Sequence
<220> FEATURE:
<223> OTHER INFORMATION: Forward primer for HCV 1b

<400> SEQUENCE: 12
agccttacag gccgggac                                                 18

<210> SEQ ID NO 13
<211> LENGTH: 18
<212> TYPE: DNA
<213> ORGANISM: Artificial Sequence
<220> FEATURE:
<223> OTHER INFORMATION: Forward primer for HCV 1b

<400> SEQUENCE: 13
agtctcacag gccgggac                                                 18

<210> SEQ ID NO 14
<211> LENGTH: 18
<212> TYPE: DNA
<213> ORGANISM: Artificial Sequence
<220> FEATURE:
<223> OTHER INFORMATION: Forward primer for HCV 1b

<400> SEQUENCE: 14
```

```
agtctcacag ggcgggac                                                  18

<210> SEQ ID NO 15
<211> LENGTH: 18
<212> TYPE: DNA
<213> ORGANISM: Artificial Sequence
<220> FEATURE:
<223> OTHER INFORMATION: Forward primer for HCV 1b

<400> SEQUENCE: 15
agcctcacag gtcgggat                                                  18

<210> SEQ ID NO 16
<211> LENGTH: 20
<212> TYPE: DNA
<213> ORGANISM: Artificial Sequence
<220> FEATURE:
<223> OTHER INFORMATION: Reverse primer for HCV 1b

<400> SEQUENCE: 16
gccacttgga atgtttgcgg                                                20

<210> SEQ ID NO 17
<211> LENGTH: 20
<212> TYPE: DNA
<213> ORGANISM: Artificial Sequence
<220> FEATURE:
<223> OTHER INFORMATION: Reverse primer for HCV 1b

<400> SEQUENCE: 17
gccacttgga atgtctgcgg                                                20

<210> SEQ ID NO 18
<211> LENGTH: 20
<212> TYPE: DNA
<213> ORGANISM: Artificial Sequence
<220> FEATURE:
<223> OTHER INFORMATION: Reverse primer for HCV 1b

<400> SEQUENCE: 18
gccacctgga atgtctgcgg                                                20

<210> SEQ ID NO 19
<211> LENGTH: 20
<212> TYPE: DNA
<213> ORGANISM: Artificial Sequence
<220> FEATURE:
<223> OTHER INFORMATION: Reverse primer for HCV 1b

<400> SEQUENCE: 19
gccacttgga atgactgcgg                                                20

<210> SEQ ID NO 20
<211> LENGTH: 20
<212> TYPE: DNA
<213> ORGANISM: Artificial Sequence
<220> FEATURE:
<223> OTHER INFORMATION: Reverse primer for HCV 1b

<400> SEQUENCE: 20
gccacttgga aagtctgcgg                                                20

<210> SEQ ID NO 21
<211> LENGTH: 26
<212> TYPE: DNA
```

```
<213> ORGANISM: Artificial Sequence
<220> FEATURE:
<223> OTHER INFORMATION: Forward primer for HCV

<400> SEQUENCE: 21
gcttgggata tgatgatgaa ctggtc                                          26

<210> SEQ ID NO 22
<211> LENGTH: 26
<212> TYPE: DNA
<213> ORGANISM: Artificial Sequence
<220> FEATURE:
<223> OTHER INFORMATION: Forward primer for HCV

<400> SEQUENCE: 22
gcgtgggata tgatgatgaa ctggtc                                          26

<210> SEQ ID NO 23
<211> LENGTH: 26
<212> TYPE: DNA
<213> ORGANISM: Artificial Sequence
<220> FEATURE:
<223> OTHER INFORMATION: Forward primer for HCV

<400> SEQUENCE: 23
gcatgggata tgatgatgaa ctggtc                                          26

<210> SEQ ID NO 24
<211> LENGTH: 26
<212> TYPE: DNA
<213> ORGANISM: Artificial Sequence
<220> FEATURE:
<223> OTHER INFORMATION: Forward primer for HCV

<400> SEQUENCE: 24
gcctgggata tgatgatgaa ctggtc                                          26

<210> SEQ ID NO 25
<211> LENGTH: 23
<212> TYPE: DNA
<213> ORGANISM: Artificial Sequence
<220> FEATURE:
<223> OTHER INFORMATION: Forward primer for HCV

<400> SEQUENCE: 25
tgggatatga tgatgaactg gtc                                             23

<210> SEQ ID NO 26
<211> LENGTH: 23
<212> TYPE: DNA
<213> ORGANISM: Artificial Sequence
<220> FEATURE:
<223> OTHER INFORMATION: Reverse primer for HCV

<400> SEQUENCE: 26
aggaacttgc cgtaggtgga gta                                             23

<210> SEQ ID NO 27
<211> LENGTH: 23
<212> TYPE: DNA
<213> ORGANISM: Artificial Sequence
<220> FEATURE:
<223> OTHER INFORMATION: Reverse primer for HCV

<400> SEQUENCE: 27
aggaacttgc cgtaggtgga ata                                             23
```

<210> SEQ ID NO 28
<211> LENGTH: 23
<212> TYPE: DNA
<213> ORGANISM: Artificial Sequence
<220> FEATURE:
<223> OTHER INFORMATION: Reverse primer for HCV

<400> SEQUENCE: 28
agaaacttgc cgtaggtgga gta                                         23

<210> SEQ ID NO 29
<211> LENGTH: 23
<212> TYPE: DNA
<213> ORGANISM: Artificial Sequence
<220> FEATURE:
<223> OTHER INFORMATION: Reverse primer for HCV

<400> SEQUENCE: 29
agaaacttgc cgtaggtgga gta                                         23

<210> SEQ ID NO 30
<211> LENGTH: 20
<212> TYPE: DNA
<213> ORGANISM: Artificial Sequence
<220> FEATURE:
<223> OTHER INFORMATION: Reverse primer for HCV

<400> SEQUENCE: 30
aggaacttgc cgtaggtgga                                             20

<210> SEQ ID NO 31
<211> LENGTH: 20
<212> TYPE: DNA
<213> ORGANISM: Artificial Sequence
<220> FEATURE:
<223> OTHER INFORMATION: Reverse primer for HCV

<400> SEQUENCE: 31
aggaacttgc cataggtgga                                             20

<210> SEQ ID NO 32
<211> LENGTH: 20
<212> TYPE: DNA
<213> ORGANISM: Artificial Sequence
<220> FEATURE:
<223> OTHER INFORMATION: Reverse primer for HCV

<400> SEQUENCE: 32
agaaacttgc cgtaggtgga                                             20

<210> SEQ ID NO 33
<211> LENGTH: 20
<212> TYPE: DNA
<213> ORGANISM: Artificial Sequence
<220> FEATURE:
<223> OTHER INFORMATION: Forward primer for HCV 1a

<400> SEQUENCE: 33
gactggccgg gacaaraacc                                             20

<210> SEQ ID NO 34
<211> LENGTH: 20
<212> TYPE: DNA
<213> ORGANISM: Artificial Sequence
<220> FEATURE:

<223> OTHER INFORMATION: Reverse primer for HCV 1a

<400> SEQUENCE: 34
gctggtggrg aggarttgtc                                               20

<210> SEQ ID NO 35
<211> LENGTH: 21
<212> TYPE: DNA
<213> ORGANISM: Artificial Sequence
<220> FEATURE:
<223> OTHER INFORMATION: Forward primer for HCV 1b

<400> SEQUENCE: 35
gtatcatcac yagcctcacr g                                             21

<210> SEQ ID NO 36
<211> LENGTH: 21
<212> TYPE: DNA
<213> ORGANISM: Artificial Sequence
<220> FEATURE:
<223> OTHER INFORMATION: Reverse primer for HCV 1b

<400> SEQUENCE: 36
cacttggaat gtytgcggta c                                             21

<210> SEQ ID NO 37
<211> LENGTH: 21
<212> TYPE: DNA
<213> ORGANISM: Artificial Sequence
<220> FEATURE:
<223> OTHER INFORMATION: Forward primer for M13

<400> SEQUENCE: 37
ttctggcgta ccgttcctgt c                                             21

<210> SEQ ID NO 38
<211> LENGTH: 23
<212> TYPE: DNA
<213> ORGANISM: Artificial Sequence
<220> FEATURE:
<223> OTHER INFORMATION: Reverse primer for M13

<400> SEQUENCE: 38
gttttcccag tcacgacgtt gta                                           23

<210> SEQ ID NO 39
<211> LENGTH: 18
<212> TYPE: DNA
<213> ORGANISM: Artificial Sequence
<220> FEATURE:
<223> OTHER INFORMATION: Forward primer for HCV 1a

<400> SEQUENCE: 39
rggrtggagr ttgytggc                                                 18

<210> SEQ ID NO 40
<211> LENGTH: 19
<212> TYPE: DNA
<213> ORGANISM: Artificial Sequence
<220> FEATURE:
<223> OTHER INFORMATION: Reverse primer for HCV 1a

<400> SEQUENCE: 40
gcyggracyt tggtgctyt                                                19

```
<210> SEQ ID NO 41
<211> LENGTH: 18
<212> TYPE: DNA
<213> ORGANISM: Artificial Sequence
<220> FEATURE:
<223> OTHER INFORMATION: Forward primer for HCV 1b

<400> SEQUENCE: 41
agyctyacag gbcgggay                                                  18

<210> SEQ ID NO 42
<211> LENGTH: 20
<212> TYPE: DNA
<213> ORGANISM: Artificial Sequence
<220> FEATURE:
<223> OTHER INFORMATION: Reverse primer for HCV 1b

<400> SEQUENCE: 42
gccacytgga awgwytgcgg                                                20

<210> SEQ ID NO 43
<211> LENGTH: 26
<212> TYPE: DNA
<213> ORGANISM: Artificial Sequence
<220> FEATURE:
<223> OTHER INFORMATION: Forward primer for HCV
<220> FEATURE:
<221> NAME/KEY: misc_feature
<222> LOCATION: (3)..(3)
<223> OTHER INFORMATION: n is a, c, g, or t

<400> SEQUENCE: 43
gcntgggata tgatgatgaa ctggtc                                         26

<210> SEQ ID NO 44
<211> LENGTH: 23
<212> TYPE: DNA
<213> ORGANISM: Artificial Sequence
<220> FEATURE:
<223> OTHER INFORMATION: Reverse primer for HCV

<400> SEQUENCE: 44
agraacttgc crtaggtgga rta                                            23

<210> SEQ ID NO 45
<211> LENGTH: 20
<212> TYPE: DNA
<213> ORGANISM: Artificial Sequence
<220> FEATURE:
<223> OTHER INFORMATION: Reverse primer for HCV

<400> SEQUENCE: 45
agraacttgc crtaggtgga                                                20
```